United States Patent

Wakabayashi et al.

Patent Number: 5,884,627
Date of Patent: Mar. 23, 1999

[54] ULTRASONIC PROBE, ULTRASONIC PROBE DEVICE. PROCESS FOR PRODUCING PIEZOELECTRIC ELEMENT FOR USE IN ULTRASONIC PROBE AND ULTRASONIC PROBE AND ULTRASONIC DIAGNOSTIC EQUIPMENT AND SYSTEM USING ULTRASONIC PROBE

[75] Inventors: Katsuhiko Wakabayashi; Yukihiko Sawada; Akiko Mizunuma, all of Hachioji, Japan

[73] Assignee: Olympus Optical Co., Ltd., Japan

[21] Appl. No.: 629,312

[22] Filed: Apr. 8, 1996

[30] Foreign Application Priority Data

Apr. 14, 1994 [JP] Japan ................................ 7-082199
Apr. 7, 1995 [JP] Japan ................................ 7-082199

[51] Int. Cl.$^6$ ........................................................ A61B 8/00

[52] U.S. Cl. ................................ 128/661.01; 128/662.03

[58] Field of Search ........................... 128/661.01, 661.1, 128/662.03; 310/334, 365, 366, 367, 368, 369

[56] References Cited

U.S. PATENT DOCUMENTS

| 4,431,936 | 2/1984 | Fu et al. | ................................ 128/661.1 |
| 5,081,995 | 1/1992 | Lu et al. | ................................ 128/662.03 |
| 5,415,175 | 5/1995 | Hanasy | ................................ 128/662.03 |

*Primary Examiner*—George Manuel
*Attorney, Agent, or Firm*—Ostrolenk, Faber, Gerb & Soffen, LLP

[57] ABSTRACT

An ultrasonic probe comprising a coaxial cable 11 capable of transferring an energizing pulse voltage and an echo signal, at least one piezoelectric element 5, an acoustic matching layer 7 disposed on a sound transmitting face side of each piezoelectric element 5 and an acoustic backing layer 8 disposed on its opposite side, the above ultrasonic probe being adapted to transmit and receive an ultrasonic wave, wherein each piezoelectric element 5 has the following distribution of spontaneous polarization according to positions of the piezoelectric element. The spontaneous polarization of the ultrasonic probe of the present invention has differences such that the spontaneous polarization is caused to be strong at a position where the absolute value of Bessel function $J_0$ (x/a) is large while the spontaneous polarization is weak at a position where the absolute value of $J_0$ (x/a) is small.

46 Claims, 27 Drawing Sheets

1: Piezoelectric ceramic

2: Full covering electrode (GND)

3: Split electrode

5: Piezoelectric element

Acoustic pressure distribution measurements

Approx. profile of sound field in example of invention

Approx. profile of sound field in example of prior art (with acoustic lens)

Approx. profile of sound field in example of prior art (without acoustic lens)

Approx. profile of radiated transmitted ultrasonic sound field viewed from A-side Approx. profile of transmitted sound field viewed from A-side Approx. profile of transmitted sound field viewed from B-side Approx. profile of spontaneous polarization distribution prior to depolarization

ULTRASONIC PROBE, ULTRASONIC PROBE DEVICE. PROCESS FOR PRODUCING PIEZOELECTRIC ELEMENT FOR USE IN ULTRASONIC PROBE AND ULTRASONIC PROBE AND ULTRASONIC DIAGNOSTIC EQUIPMENT AND SYSTEM USING ULTRASONIC PROBE

BACKGROUND OF THE INVENTION

1. Field of the Invention

The present invention relates to an ultrasonic probe and ultrasonic probe device for use in, for example, ultrasonic endoscopes employed for medical purposes, a process for producing a piezoelectric element for use in such an ultrasonic probe and an ultrasonic diagnostic equipment and system using such an ultrasonic probe.

2. Discussion of Related Art

The common structure of conventional ultrasonic probes is as shown on page 186 of "Handbook of Medical Ultrasonic Equipments" edited by Electronic Industries Association of Japan (corporate juridical person) and published by Corona Publishing Co., Ltd., Tokyo, Japan, and they are fabricated by bonding a piezoelectric element composed of a piezoelectric ceramic plate as represented by PZT whose two principal surfaces are provided with a pair of electrodes to an acoustic backing layer and further bonding an acoustic matching layer and an acoustic lens thereto.

In this ultrasonic probe, a pulser applies pulsed energizing voltage of about one hundred or hundreds of volts to the above piezoelectric element, so that a rapid morphology change is caused to occur by the converse piezoelectric effect of the piezoelectric element. The resultant vibration is transmitted through the acoustic matching layer and the acoustic lens to thereby effectively transmit pulses toward an object to be observed. The transmitted pulses are reflected at each tissue interface of the body in medical uses or at a noncontinuous part such as any of various defects inside an object to be examined in nondestructive inspections and retransmitted through the acoustic lens and the acoustic matching layer to thereby apply mechanical vibration to the piezoelectric element. This mechanical vibration is converted to electrical signal by the piezoelectric effect of the piezoelectric element, which is observed by means of a diagnostic equipment.

Various methods are available for enhancing the resolution in the imaging, which include modifying the acoustic lens and the pattern of the electrode of the piezoelectric element and curving the surface of the piezoelectric element itself so as to slenderize the transmitted ultrasonic beam. Further, an annular array sound field forming is being tried in which the electrode is split into several parts to thereby cause applied energizing pulse voltages to have differences.

Moreover, with respect to the ultrasonic probe, for example, an invention is noted which is described in Japanese Patent Application Laid-Open Specification No. 111198/1990. In this invention, for example, a full covering electrode 152 is disposed on one side of a piezoelectric ceramic 151 while split electrodes 153a, 153b, 153c are disposed on the other side of the piezoelectric ceramic as shown in FIGS. 47 and 48. Thus, the invention provides a piezoelectric element 154 in which, with respect to the distribution of polarization intensity, the central split electrode 153a has a strong spontaneous polarization, the spontaneous polarization becoming weaker as the distance to the peripheral split electrode 153c is decreased, and also provides an ultrasonic probe including this piezoelectric element 154.

However, all the conventional methods of improving the resolution of an ultrasonic image of the ultrasonic probe have had respective advantages and disadvantages. In particular, the ultrasonic probe including an acoustic lens or a piezoelectric element that has a curving, especially concave, surface advantageous in that the ultrasonic beam is slenderized near the focus to thereby enable obtaining an image of high resolution but has a drawback in that the beam width is enlarged as the distance from the focus is increased to thereby deteriorate the image quality. Accordingly, the optimum observation distance permitting practical observation becomes unfavorably small.

In this connection, measuring the sound field of ultrasonic beam transmitted from the ultrasonic probe and determining the beam width thereof demonstrates that the region where the beam width is small is extremely reduced so that the optimum observation distance (depth of focus) permitting practical observation is small as shown in FIG. 49 (in FIG. 49, the axis of abscissa represents the distance X (mm) between the face transmitting ultrasonic beam and the measuring point while the axis of ordinate represents the beam width (mm) at the measuring point; the above beam width means the portion of at least 50% (−6 dB) of the maximum acoustic pressure in a plane at right angles to the beam axis, the beam width meaning the diameter of the area thereof).

In the use of the ultrasonic probe of the annular array type, it is known that the focusing point of ultrasonic beam can be changed (the depth of focus can be increased) by, for example, providing a plurality of pulsers or devising the circuit to thereby control the phase of voltage applied to each ring-shaped electrode.

That is, the ultrasonic wave can be converged so as to focus on a point to be observed to thereby enable clear observation of the point. Further, it is feasible to repeat ultrasonic wave transmission and receiving a plurality of times while changing the focal length and synthesize received signals so that a clear image is obtained in a wide range.

However, in the above method, a plurality of leads must be connected to the piezoelectric element. Complete shielding is required for avoiding the entry of noise between the plurality of leads. This is disadvantageous from the viewpoint of the reduction of the diameter of the ultrasonic probe for use in medical applications and the like. Further, there is the problem that the requirement for a complex electrical circuit capable of phase control as mentioned above would cause a huge increase of the cost of the diagnostic equipment.

In the method comprising repeating transmission and receiving while changing the focal length and synthesizing a plurality of received signals, the time required for gaining a sheet of image is increased, so that the frame rate (number of images per time) is lowered. Consequently, the problem occurs that the image is fluctuated by, for example, the somatic movement, respiration or heart beat of the examinee to thereby disenable satisfactory diagnosis.

In the use of a concave transducer as another usage of the annular array type, a technique is available such that all parts are simultaneously driven at the time of transmission to thereby transmit ultrasonic wave while the area of receiving parts is increased in accordance with the observation distance at the time of receiving to thereby attain enhanced resolution. However, as in the above method, this technique encounters problems such that not only is the wiring complex to thereby render production difficult but also the electrical circuit such as an adder circuit becomes complex so that high cost and lowered reliability would result.

Distributing the ultrasonic wave transmitted by an ultrasonic transducer so as to be strong in the center and weak in the periphery enables reducing the side lobe, i.e., transmission of ultrasonic wave in essentially unintended directions. It is known that the side lobe reducing effect is especially high when a provided acoustic pressure distribution has a graphical profile of the normal distribution (Gaussian distribution). The object of the invention of Japanese Patent Application Laid-Open Specification No. 111198/1990 is directed toward this effect, but the invention has drawbacks in that there is no effect of focusing ultrasonic wave with the optimum observation distance being small.

It is known that distributing the ultrasonic wave transmitted by an ultrasonic transducer in a profile of the zeroth-order Bessel function would cause the ultrasonic wave to become diffractionless ultrasonic beam, i.e., wave being propagated without diffusion. The use of the thus obtained diffractionless ultrasonic beam enables obtaining image produced by ultrasonic beam of uniform width from near the ultrasonic transducer to a position distant therefrom. That is, image of line focus can be obtained realizing clear focusing from near the ultrasonic transducer to a position distant therefrom.

The method was reported for realizing the above ultrasonic beam, in which use is made of a piezoelectric element provided with concentric multi-ring electrodes to each of which a driving circuit is connected by means of cables and in which the energizing pulse voltage applied to each electrode ring is distributed in a Bessel profile. However, in this method, a plurality of cables must be connected to the piezoelectric element. Complete shielding is required for avoiding the entry of noise between the plurality of cables. This is disadvantageous from the viewpoint of the reduction of the diameter of the ultrasonic probe for use in medical applications, especially, applications inside the body cavity. Further, there is the problem that the requirement for a complex electrical circuit capable of effecting voltage and phase controls would cause a grave increase of the cost of the diagnostic equipment.

The following reference describes a method of fabricating a piezoelectric element of the Bessel polarization type which has similarity to the piezoelectric element for use in the present invention:

- title: Bessel beam ultrasonic transducer: Fabrication method and experimental results,
- authors: D. K. Hsu, F. J. Margetan and D. O. Thompson, and
- publication: Appl. Phys. Lett. 55(20), 13 Nov. 1989, pp 2066–2068.

The above reference employs the following method in which:

- a piezoelectric element is fabricated which is provided with two concentric circular grooves of different depths and a central cavity,
- polarization is effected by the application of polarization voltages having polarities different between the grooves and the face opposite thereto; at that time, mutually neighboring grooves and cavity have respective voltages of different polarities applied thereto, and
- the grooves are polished to thereby remove the same, so that a flat piezoelectric element is obtained.

However, the piezoelectric element obtained by the method of this reference has drawbacks in that:

- polarization voltage is applied not only between the electrodes opposite to each other with the piezoelectric element interposed therebetween but also between the electrodes neighboring to each other, so that the occurrence of part 155 polarized parallel to a principal surface of the piezoelectric element 154 as shown in FIG. 50 is inevitable with the result that undesired vibration is likely to occur at the time of driving with voltage applied to thereby transmit ultrasonic wave of undesired frequency in undesired directions, which generates virtual image attributed to artifacts on the ultrasonic image to thereby deteriorate the quality of the ultrasonic image, and
- major portion of the piezoelectric element is polished away after the polarization, so that the fabrication time is prolonged and that the yield becomes poor because of the required grooving and polishing after the polarization.

SUMMARY OF THE INVENTION

An object of the present invention is to provide an ultrasonic probe characterized in being small in the number of parts, especially, the number of cables and so structured as to obtain a nondiffracting sound field of the Bessel type with the use of a transducer to thereby uniform the width of the ultrasonic beam and increase the depth of focus of an ultrasonic image. The ultrasonic probe enables obtaining clear image from near the ultrasonic probe device to a part distant therefrom and thus enables rapidly conducting accurate diagnosis.

Another object of the present invention is to provide a piezoelectric element for an ultrasonic probe of high resolution enabling forming the sound field, attaining a line focusing and use with a relatively simple electrical circuit by the employment of a piezoelectric element having its polarization intensity partially weakened on the basis of the Bessel function.

A further object of the present invention is to provide a process for producing an ultrasonic probe of high resolution enabling forming the sound field, attaining a line focusing (increasing the depth of focus) and use with a relatively simple electrical circuit by the employment of a piezoelectric element having its polarization intensity weighted on the basis of the Bessel function.

Still a further object of the present invention is to provide an ultrasonic diagnostic equipment and an ultrasonic diagnostic system each including the above ultrasonic probe.

The foregoing and other objects, features and advantages of the present invention will become apparent from the following detailed description and appended claims taken in connection with the accompanying drawings.

DETAILED DESCRIPTION OF THE INVENTION

Figure 1:
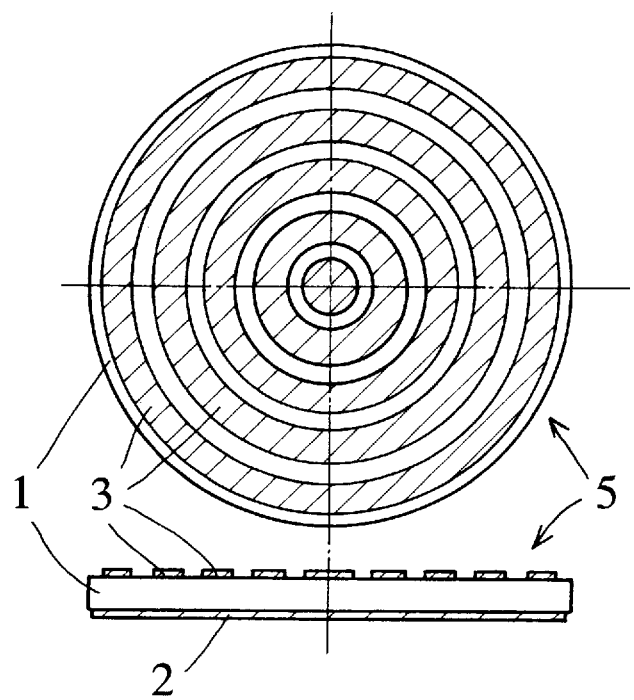
FIG. 1 is a plan and sectional view of the piezoelectric element of Embodiment 1 of the present invention.

In one aspect of the present invention, there is provided an ultrasonic probe comprising a cable capable of transferring an energizing pulse voltage and an echo signal, at least one piezoelectric element, an acoustic matching layer disposed on a sound transmitting face side of each piezoelectric element and an acoustic backing layer disposed on its opposite side, the above ultrasonic probe being adapted to transmit and receive an ultrasonic wave, wherein each piezoelectric element has two principal surfaces provided with respective electrodes electrically connected with the cable, and wherein each piezoelectric element has differences in intensity of spontaneous polarization according to positions of the piezoelectric element as defined below:

a distribution of the intensity of spontaneous polarization is determined so that an acoustic pressure distribution from the probe is as follows:

provided that a straight line at right angles to a geometric symmetry axis is selected on a surface of the piezoelectric element and designated as X-axis, the above X-axis having an origin which is an intersection of the X-axis and the geometric symmetry axis of the piezoelectric element, the zeroth-order Bessel function $Y=J_0(x/a)$, wherein a is an arbitrary constant, is drawn along the above X-axis, so that the value of $J_0(x/a)$ at each position of the X-axis is caused to correspond to a sign (positive or negative) and magnitude of acoustic pressure transmitted from the position upon application of an energizing pulse, namely, the spontaneous polarization is caused to be strong at a position where the absolute value of $J_0(x/a)$ is large while the spontaneous polarization is weak at a position where the absolute value of $J_0(x/a)$ is small, so that the spontaneous polarization at a position where the $J_0(x/a)$ is positive has a direction opposite to that of the spontaneous polarization at a position where the $J_0(x/a)$ is negative, so that the piezoelectric element has a distribution of intensity of spontaneous polarization which is linearly symmetrical or axially symmetrical on its axis of symmetry, and so that the direction of the spontaneous polarization is substantially perpendicular to the two principal surfaces throughout the surfaces of the piezoelectric element. The direction and magnitude of the spontaneous polarization are represented by the direction and magnitude of each arrow shown on the piezoelectric element (piezoelectric ceramic) 1 in FIG. 2.

In another aspect of the present invention, there is provided an ultrasonic probe comprising a cable capable of transferring an energizing pulse voltage and an echo signal, at least one piezoelectric element, a sound matching layer disposed on a sound transmitting face side of each piezoelectric element and an acoustic backing layer disposed on its opposite side, the above ultrasonic probe being adapted to transmit and receive an ultrasonic wave, wherein each piezoelectric element has differences in intensity of spontaneous polarization according to positions of the piezoelectric element, the above spontaneous polarization having a direction substantially perpendicular to two principal surfaces throughout the surfaces of the piezoelectric element, and wherein a distribution of the intensity of spontaneous polarization is determined so that an acoustic pressure distribution from the probe is as follows:

provided that a straight line at right angles to a geometric symmetry axis is selected on a surface of the piezoelectric element and designated as X-axis, the above X-axis having an origin which is an intersection of the X-axis and the geometric symmetry axis of the piezoelectric element, the zeroth-order Bessel function $Y=J_0(x/a)$, wherein a is an arbitrary constant, is drawn along the above X-axis, the above Bessel function being step approximated so that the step approximated value of $J_0(x/a)$ at each position of the X-axis is caused to correspond to a sign (positive or negative) and magnitude of acoustic pressure transmitted from the position upon application of an energizing pulse, namely, the spontaneous polarization is caused to be strong at a position where the step approximated value of $J_0(x/a)$ is large while the spontaneous polarization is weak at a position where the step approximated value of $J_0(x/a)$ is small, so that the spontaneous polarization at a position where the step approximated $J_0(x/a)$ is positive has a direction opposite to that of the spontaneous polarization at a position where the step approximated $J_0(x/a)$ is negative, and so that the piezoelectric element has a distribution of intensity of spontaneous polarization which is linearly symmetrical or axially symmetrical on its axis of symmetry.

In the ultrasonic probe of the present invention, the electrode may be split on at least one surface of the piezoelectric element at the time of the above polarization, the split electrode parts on the identical surface being connected after the polarization.

Further, in the ultrasonic probe of the present invention, use may be made of a piezoelectric element in which the electrode is not present on at least one surface thereof at a position where the value of spontaneous polarization is nil in the distribution of spontaneous polarization intensity based on the Bessel function or at its vicinity.

The relationship between the direction and magnitude of the spontaneous polarization of the piezoelectric element 1 as a member of the ultrasonic probe of the present invention and the sound transmitted therefrom is as described below. The extent of deformation of the piezoelectric element exhibited upon application of a given direct current voltage is determined in conformity to the intensity of spontaneous polarization. Further, the direction of deformation of the piezoelectric element is determined by the direction of spontaneous polarization. Thus, application of the identical energizing pulse voltage to all the surface of the piezoelectric element having a distribution of spontaneous polarization intensity enables obtaining ultrasonic wave front with a profile conforming to the distribution of spontaneous polarization intensity.

The polarization intensity of the piezoelectric element for use in the ultrasonic probe can be weighted in the form of the Bessel function by partially changing the polarization voltage. The ultrasonic probe including this piezoelectric transducer can transmit artificial Bessel beam to an object to be observed through the acoustic matching layer. The Bessel beam is a nondiffracting wave which does not diffuse during the propagation and the pulse transmitted from the ultrasonic probe propagates without any significant scattering.

In the present invention, on at least one surface of the piezoelectric element, the electrode may be split along the distribution of spontaneous polarization intensity based on the above assumed Bessel function, followed by application of the polarization voltage to each electrode to thereby effect the polarization so as to have the spontaneous polarization intensity conforming to the Bessel function.

In addition to the above function, in the present invention, the ultrasonic probe may be composed of the piezoelectric element obtained by splitting the electrode on at least one surface of the piezoelectric element at the time of polarization thereof, applying respective voltages different from each other to the split electrode parts so that the electrode parts have respective polarization intensities varied from each other and conducting electrode connection or formation to thereby obtain the piezoelectric element which can be driven by a single coaxial cable.

In the piezoelectric element of the present invention, the electrode pattern may be designed so that on at least one surface of the piezoelectric element the electrode is not present at a zone where the value of the Bessel function of the piezoelectric element is equivalent to zero or at its vicinity with the result that the vibration fundamentally does not occur around the zone.

That is, in the piezoelectric element for use in the ultrasonic probe of the present invention, the magnitude of spontaneous polarization may be provided with differences according to positions of the piezoelectric element by performing partial depolarization of the previously polarized piezoelectric element in conformity to the Bessel function.

The ultrasonic probe of the present invention has the following function. Illustratively, the polarization intensity of the piezoelectric element for the ultrasonic probe may partially be depolarized by heating to thereby execute weighting of the polarization intensity in the form of the Bessel function. The ultrasonic probe including this piezoelectric element enables transmitting artificial Bessel beam to an object to be observed. The Bessel beam is a nondiffracting wave and the pulse transmitted from the ultrasonic probe propagates without any significant scattering.

In an additional aspect of the present invention, there is provided an ultrasonic diagnostic equipment comprising an ultrasonic probe to which energizing pulses of identical polarity and voltage are applied with varied timings to thereby conduct electronic focusing.

In a further aspect of the present invention, there is provided an ultrasonic diagnostic equipment having an electronic linear scanning ultrasonic probe connected thereto in which energizing pulses of varied polarity and magnitude are applied with identical timings to a plurality of piezoelectric elements used for forming a single acoustic beam.

In still a further aspect of the present invention, there is provided an ultrasonic diagnostic system comprising an ultrasonic probe wherein, as a small element forming the ultrasonic probe, use is made of a piezoelectric element of a rectangular shape having its intensity of spontaneous polarization determined as follows:

provided that the Bessel function of $J_0(x/a)$ (wherein a is a constant) is set on an axis parallel to a side of one small element of each piezoelectric element with the assumption of X-axis of coordinate having its origin at an middle point of the above side of the small element, spontaneous polarization is given so that an acoustic pressure distributed in a profile resulting from parallel movement of the Bessel function along another side of the small element is obtained, and wherein application of a transmitting acoustic pressure to each element of a block forming a single acoustic beam with the use of the ultrasonic probe is performed as described later.

In still a further aspect of the present invention, there is provided a process for producing the piezoelectric element having a Bessel distribution of polarization intensity as described above, which comprises polarizing a piezoelectric element to saturation followed by partial depolarization.

PREFERRED EMBODIMENT OF THE INVENTION

The present invention will now be described in greater detail with reference to the following Embodiments, which should not be construed as limiting the scope of the invention.

Embodiment 1

Embodiment 1 of the present invention will be described with reference to FIGS. 1 to 20.

Figure 2:
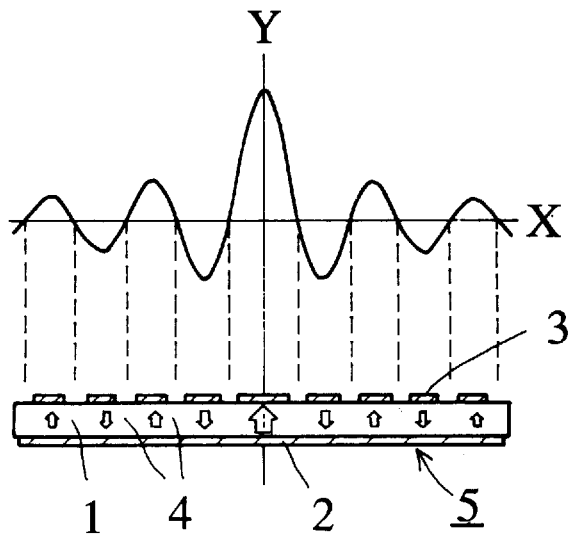
FIG. 2 is a view showing the positional relationship between the Bessel function and the electrode of the piezoelectric element according to Embodiment 1.
Figure 3:
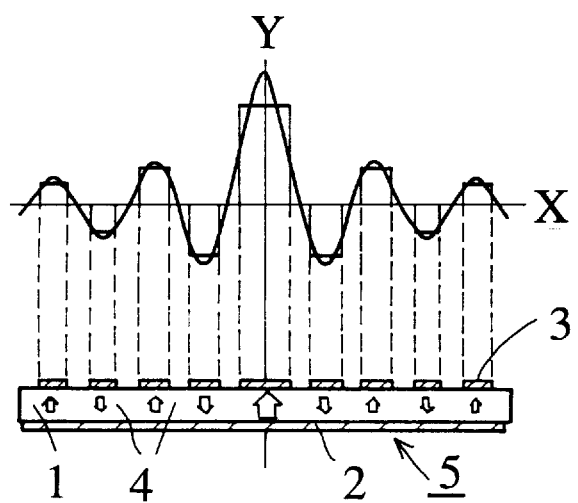
FIG. 3 is a view showing the positional relationship between the Bessel function and the electrode of the piezoelectric element and the direction and intensity of polarization according to Embodiment 1.
Figure 4:
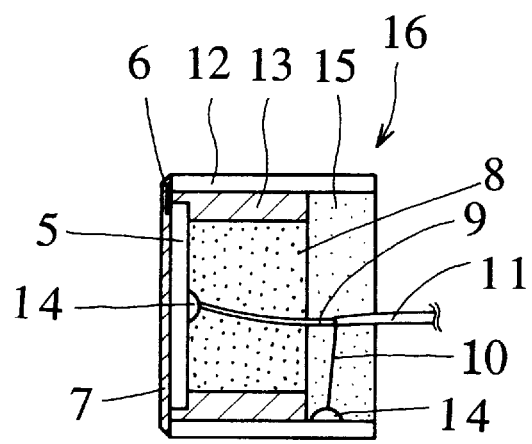
FIG. 4 is a sectional view of a transducer part according to Embodiment 1.
Figure 5:
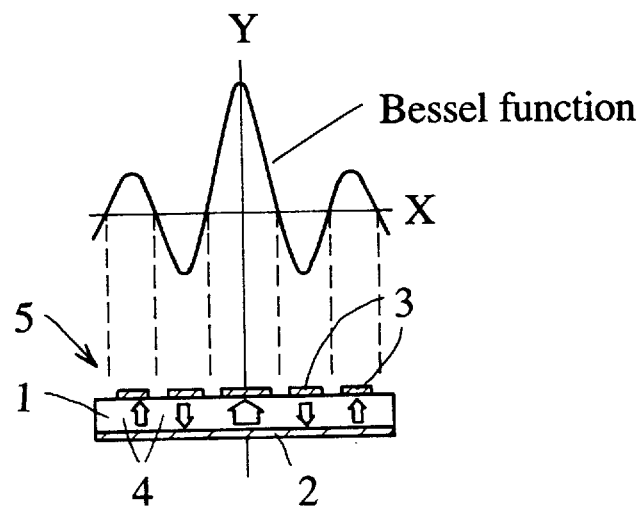
FIG. 5 is a view showing the positional relationship between the Bessel function and the electrode of the piezoelectric element and the direction and intensity of polarization according to Embodiment 1.
Figure 6:
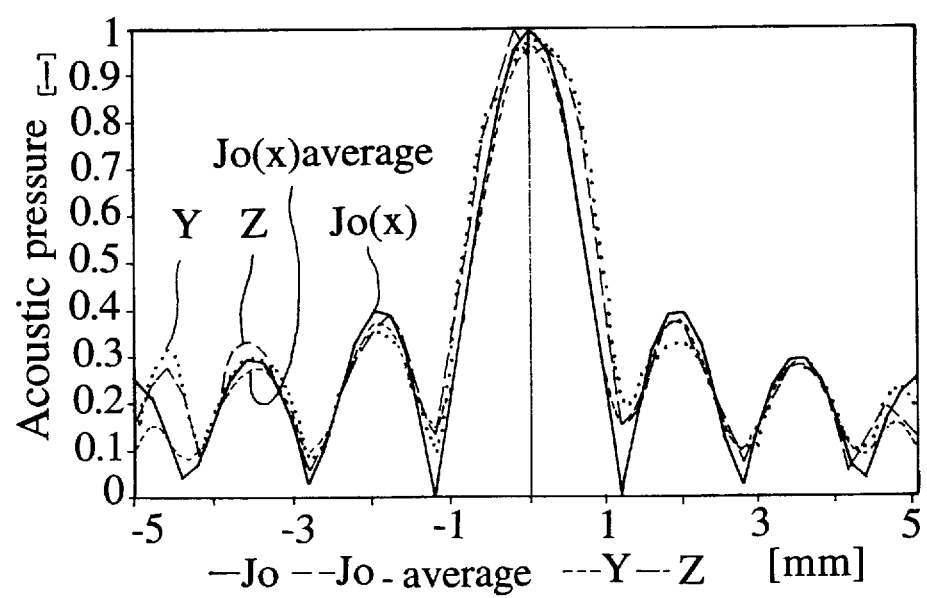
FIG. 6 is a graph of the acoustic pressure distribution of the ultrasonic probe according to Embodiment 1.
Figure 7:
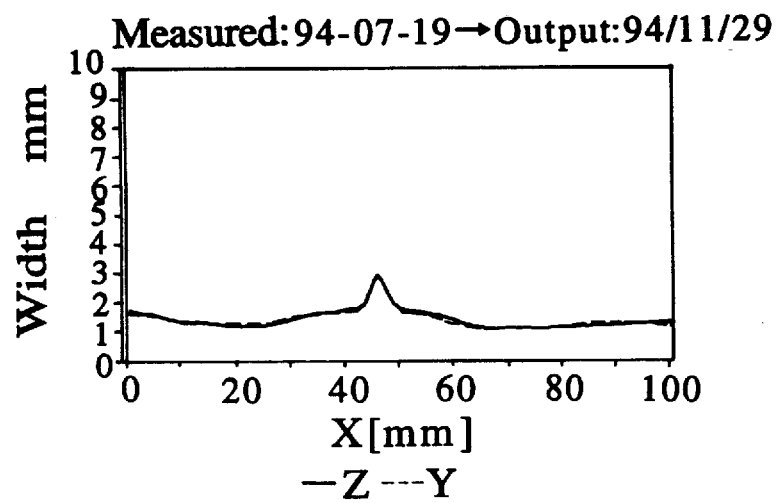
FIG. 7 is a graph of the beam width according to Embodiment 1.
Figure 8:
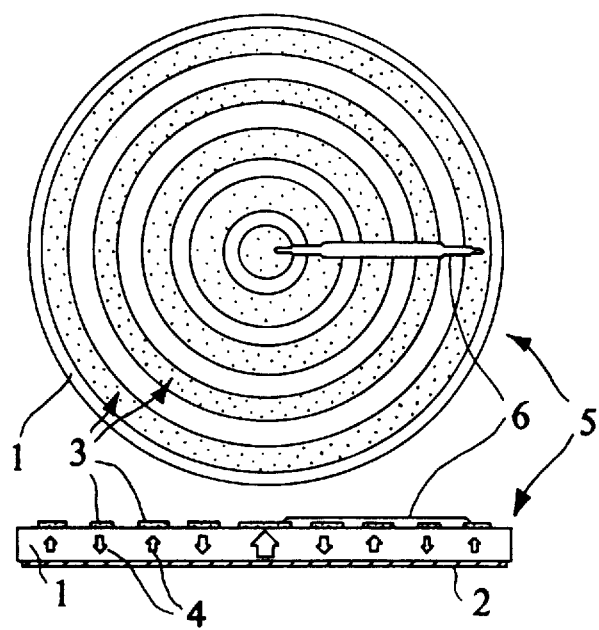
FIG. 8 is a view showing the connection of split electrodes according to Embodiment 1.
Figure 9:
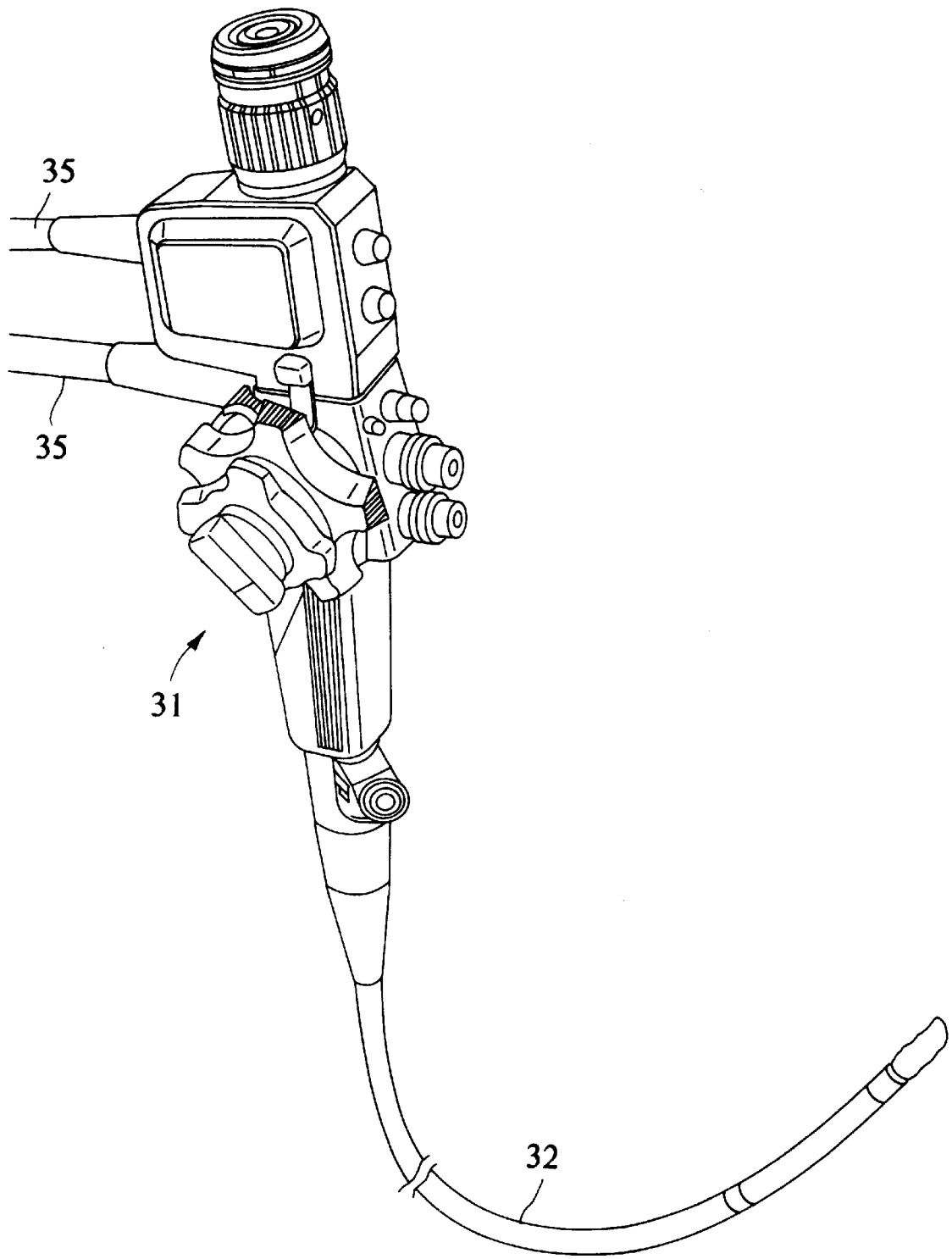
FIG. 9 is a view showing the ultrasonic endoscope including the ultrasonic probe according to Embodiment 1.
Figure 49:
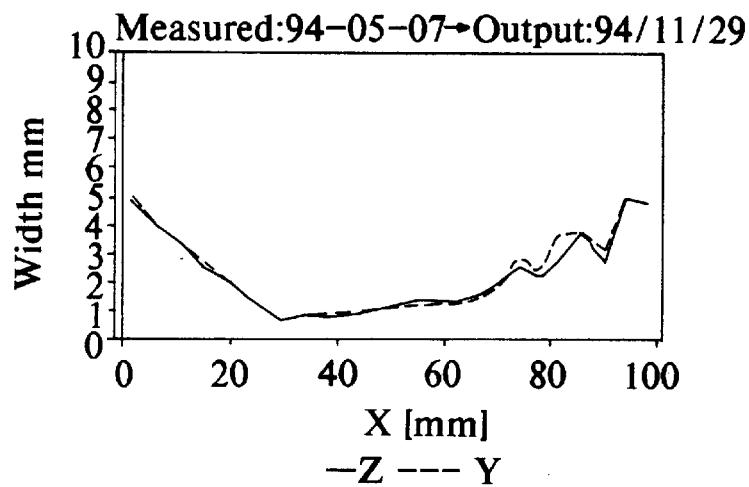
FIG. 49 is a graph showing the beam width of the transducer 7 including the conventional piezoelectric element.
Figure 50:
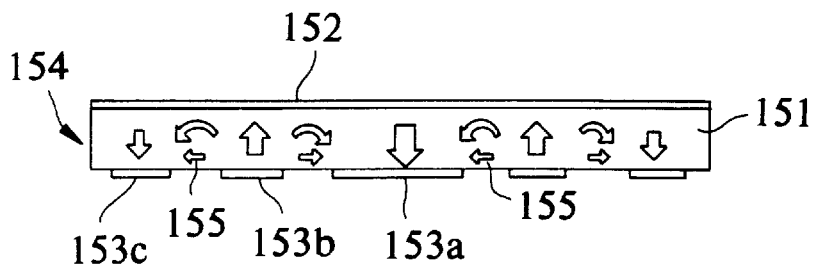
FIG. 50 is a view showing the state of polarization of the conventional piezoelectric element.

As mentioned above, FIG. 1 is a plan and sectional view of a piezoelectric ceramic 1 structuring a piezoelectric element 5; FIG. 2 is a sectional view showing the positional relationship between the Bessel function and split electrodes of the piezoelectric element 5; FIG. 3 is a view showing the positional relationship between the Bessel function and the split electrodes of the piezoelectric element 5 together with the direction and intensity of polarization; FIG. 4 is a sectional view of a transducer part of the ultrasonic probe; FIG. 5 is a view showing the piezoelectric element and the position of split electrodes and the direction and intensity of polarization thereof; FIG. 6 is a graph of the acoustic pressure distribution in the vicinity of a sound transmitting face of the ultrasonic probe; FIG. 7 is a graph of the beam width as is FIG. 49; FIG. 8 is a view showing the connection of the split electrodes of the piezoelectric element 5 effected by means of a conductive resin; and FIG. 9 is a view showing the ultrasonic endoscope including the ultrasonic probe according to Embodiment 1.

First, a lapped base of 10 mm in diameter and 160 μm in thickness composed of a PZT material is provided as the piezoelectric ceramic 1 structuring the piezoelectric element 5. Silver paste is applied to the entirety of one principal surface of this base to form a full covering electrode 2 and split electrodes 3 are printed and baked in the form of concentric multi-rings on the other principal surface. The split electrodes 3 having the form of concentric multi-rings are those patterned on the basis of the zeroth-order Bessel function as shown in FIG. 2 and are so structured as to have no split electrode 3 near Y=0 of the X-Y coordinate system. The piezoelectric element 5 whose one side has the split electrodes 3 made in the form of multi-rings has been polarized under the following conditions. Initially, the values of a zone of the Bessel function corresponding to each electrode are averaged as shown in FIG. 3, and the polarization proportion is determined so that the acoustic pressure is transmitted as shown in the same graph as the Bessel function of FIG. 2.

The polarization is carried out by changing the polarization voltage by means of each split electrode 3 so that the piezoelectric constant $d_{33}$ is obtained conforming to the above average. The polarization is conducted in a silicone bath of 80° C. in accordance with the piezoelectric constant $d_{33}$ previously determined for each material and the polarization voltage. The state of polarization has been checked on the basis of easily measurable coupling coefficient $K_{33}$ with reference to the relationship between coupling coefficient $K_{33}$ and piezoelectric constant $d_{33}$ having been confirmed by advance experiments. With respect to a zone where the Bessel function has a negative value, the polarization is executed with the polarization direction conversed.

The electrodes 3 on one side of the thus obtained piezoelectric element 5 are connected to each other by a conductive resin 6 as shown in FIG. 8. Referring to FIG. 4, the piezoelectric element 5 is secured to a housing 12 of SUS through an insulating barrel 13 so that the split electrodes 3 are set inside. The full covering electrode 2 disposed on a front side is connected to the housing 12 by the use of the conductive resin 6. Thereafter, an acoustic matching layer 7 of 60 μm in thickness composed of an epoxy resin is formed on the surface of the front-side full covering electrode 2. A signal line 9 and a shild line 10 of a coaxial cable 11 are connected by solder 14 or the like to a part of the electrodes 3 split in the form of multi-rings and the housing 12, respectively. An acoustic backing layer 8 composed of a mixture of an epoxy resin and tungsten is cast on the side of the electrodes 3 split in the form of multi-rings, thereby obtaining a transducer part 16 for use in a ultrasonic probe as shown in FIG. 4.

Figure 10:
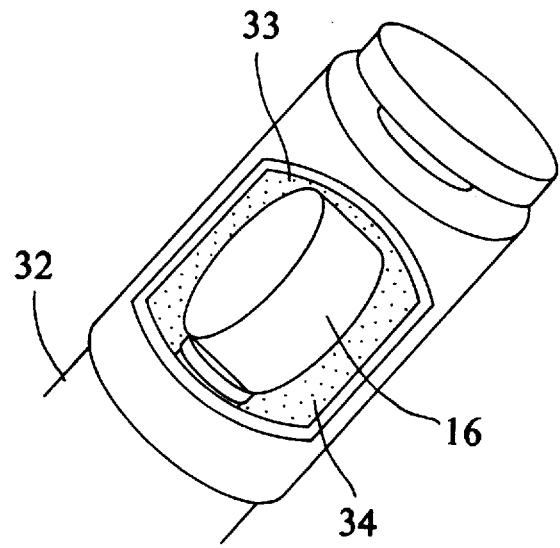
FIG. 10 is a partial enlarged view showing the transducer part assembled in the ultrasonic endoscope of FIG. 10.

An ultrasonic endoscope including the transducer part 16 is shown in FIG. 9. This ultrasonic endoscope has an operating part 31 to be held by an operator connected to a flexible insertion part 32. The operating part 31 is connected to an ultrasonic diagnostic device and a light source both not shown by means of cords 35. An enlarged view of the state of the tip of the above insertion part 32 is shown in FIG. 10. An acoustic window 33 is disposed at the tip of the insertion part 32. The acoustic window 33 is formed of a thin hard polyethylene of about 0.2 mm in thickness. The acoustic window 33 is watertightly sealed and the above transducer part 16 is rotatably arranged thereinside. The hollow inside the acoustic window 33 is filled with an acoustic coupling medium 34. Usually, water is used as the acoustic coupling medium 34.

The operator inserts the insertion part 32 in the body cavity of an examinee as in the use of the conventional ultrasonic endoscope to thereby conduct optical observation and ultrasonic diagnosis. When the ultrasonic diagnosis is conducted, not only is the transducer part 16 rotated by the use of the operating part 31 or a switch mounted on the ultrasonic diagnostic unit not shown but also energizing pulses are applied by a pulser not shown which is arranged in the diagnostic equipment. The energizing pulses are applied through the above coaxial cable 11 to the piezoelectric element 1.

A section of the piezoelectric ceramic 1 produced by the above illustrated procedure has polarization direction and intensity as shown in a lower side of FIG. 2, thereby showing a piezoelectric element. Specifically, the intensity of the spontaneous polarization 4 is high around the center of the split electrodes 3, and the smaller the distance to the periphery, the lower the intensity of the spontaneous polarization 4 between split electrodes 3. Application of uniform voltage to the entire surface of the above piezoelectric ceramic 1 being the piezoelectric element leads to the increase of deformation at a part where the polarization intensity is high and to the determination of deformation direction depending on the direction of polarization and the polarity of applied voltage.

Determination of the arrangement of split electrodes 3 on the piezoelectric ceramic 1 structuring the piezoelectric element 5 on the basis of the Bessel function, preparation of the transducer part 16 of the ultrasonic probe as shown in FIG. 4 with the use of the piezoelectric ceramic 1 provided with differences in polarization intensity and application of energizing pulses to the piezoelectric element 5 with the use of the pulser not shown according to Embodiment 1 cause the transmitted ultrasonic beam to approximate to the Bessel function.

In accordance with the principle as described above, application of energizing pulses to the piezoelectric element 5 leads to transmission of pulses with an acoustic pressure distribution having the form of the Bessel function. As mentioned hereinbefore, the ultrasonic wave with an acoustic pressure distribution having the form of the Bessel function is a nondiffracting ultrasonic beam, i.e., a wave propagating without diffusion. The transmitted ultrasonic beam propagates through the acoustic coupling medium 34 and the acoustic window 33 toward inside the body of the examinee in uniform beam width. Water in which the acoustic velocity is substantially equal to that in the organism is used as the acoustic coupling medium 34, and a thin hard polyethylene is used in the acoustic window 33 in order to increase the transmittance for the ultrasonic beam, so that the attenuation and sound field disorder of the ultrasonic beam passing through these are on negligible levels.

The directivity characteristic at the time of receiving is similar to that at the time of transmission, so that reflected echoes from regions of substantially uniform size are effectively received as in the transmitted sound field.

The use of the thus obtained ultrasonic beam enables obtaining ultrasonic image by the transmission and receiving of ultrasonic beam of substantially uniform beam width from near the ultrasonic transducer to a position distant therefrom. That is, image of line focus can be obtained realizing clear focusing from near the ultrasonic transducer to a position distant therefrom.

The application of energizing pulses by the pulser to the ultrasonic transducer part 16 including the piezoelectric ceramic 1 as shown in FIG. 5 causes the acoustic pressure distribution of pulses transmitted near the acoustic matching layer 7 to approximate to the Bessel function.

The results of measurement of the ultrasonic acoustic pressure distribution conducted with the use of a hydrophone in the vicinity (distance of about 1 mm) of the above acoustic matching layer 7 are shown in FIG. 6. In FIG. 6, the absolute value of Bessel function $J_0(x)$, the calculated value, $J_0(x)$ average, obtained by averaging the calculated $J_0(x)$ by hydrophone's active element area to simulate measurement of the acoustic pressure distribution of the Bessel function form by means of a hydrophone and the results of measurement (Y, Z) of acoustic pressure are shown on two axes crossing at right angles to each other. It is seen that the actual transmitted acoustic pressure is very approximate to the calculated value $J_0(x)$ average. Herein, x means the distance from the axis of symmetry of the transducer part 16.

The relationship between $J_0(x)$ and $J_0(x)$ average will be described as follows.

The hydrophone includes a circular active element sized so as to have a diameter of about 0.6 mm. Consequently, what is actually measured by the hydrophone is not the acoustic pressure at one point but the average acoustic pressure at the sound receiving part. Thus, when a complex sound field distribution is measured by the hydrophone, a distribution smoother than the actual one is measured. $J_0(x)$ average of FIG. 6 is the calculated Bessel distribution of sound field obtained from measurements averaged every 0.6 mm of diameter.

The Bessel beam is known as a nondiffracting beam. Measuring the sound field of the transducer part 16 according to Embodiment 1 and measuring the beam width demonstrate the uniformity of the width of the ultrasonic beam as shown in FIG. 7 (the axis of abscissa indicates the distance, X mm, between the ultrasonic beam transmitting surface and the measuring point while the axis of ordinate indicates the beam width, mm, at the measuring point), thereby ensuring the fabrication of an ultrasonic probe having a large optimum observation distance (depth of focus) having never been attained in the art. Therefore, an ultrasonic probe of high resolution can be fabricated in which use is made of a single coaxial cable and a single pulser so that the electrical circuit and the transducer part 16 have simple structures and are inexpensive.

The ultrasonic diagnostic equipment is the same as the conventional one, so that effective utilization of the existent equipment can be attained.

Figure 11:
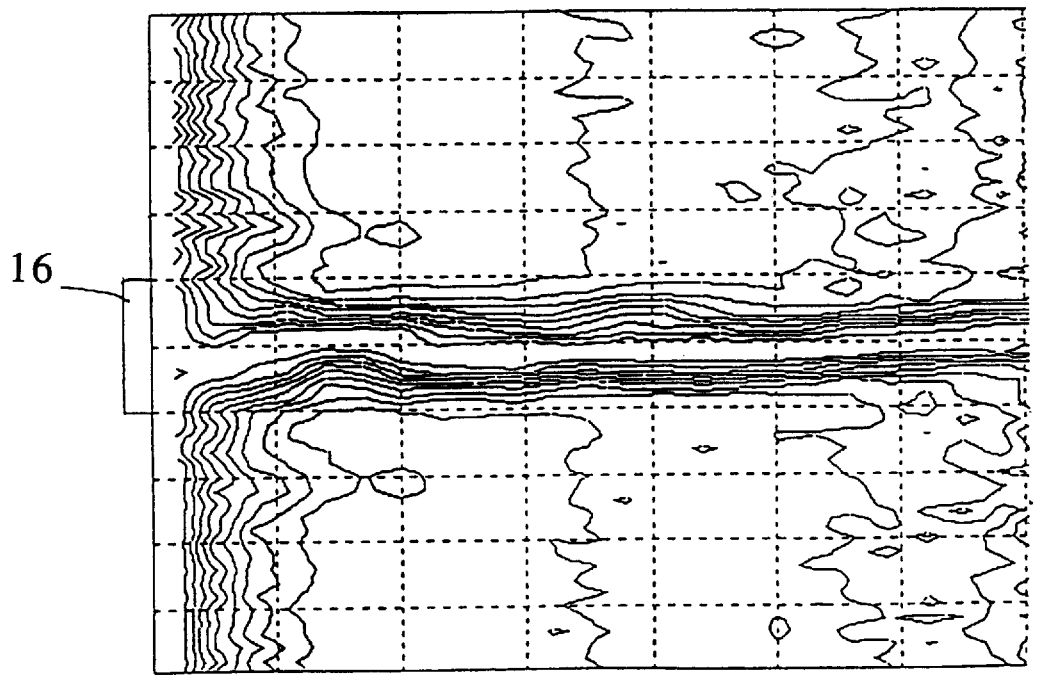
FIG. 11 is an explanatory view of measurements of acoustic pressure distribution of the ultrasonic probe according to Embodiment 1.

FIG. 11 shows measurements of acoustic pressure transmitted from the transducer part 16 of the ultrasonic probe of Embodiment 1. The ultrasonic sound field formed by disposing the transducer part 16 at a left edge of FIG. 11 and applying energizing pulses to effect transmission has actually been measured by the use of a hydrophone of 0.6 mm in effective diameter. The acoustic pressure data has been exhibited by a contour obtained by rendering the same dimensionless with the acoustic pressure on the acoustic axis for each line perpendicular to the acoustic axis. Continuation of a central high acoustic pressure part in substantially fixed width is seen.

Figure 12:
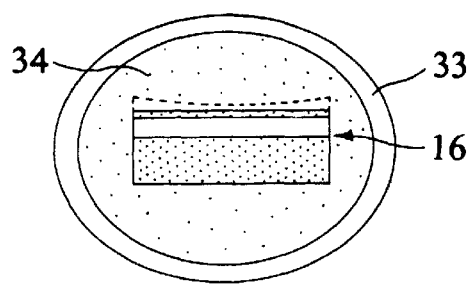
FIG. 12 is an explanatory view of sound field profiles of the ultrasonic probes according to Embodiment 1 and the prior art.

FIG. 12 shows a conceptual view of the effect of Embodiment 1. FIG. 12 is a sectional view of a face taken perpendicularly to the axis of the insertion part 32 of the ultrasonic endoscope including the transducer part 16 of the ultrasonic probe. The approximate pattern profile of the sound field transmitted from the acoustic window 33 of each of the ultrasonic endoscopes according to Embodiment 1 and the prior art is shown in FIG. 12. The prior art has included one in which an acoustic lens has been arranged on a sound transmitting face side of the piezoelectric ceramic to thereby converge the ultrasonic wave and another in which no acoustic lens has been mounted. Although the width of the ultrasonic beam at the position where the sound field is most converged is smaller in the prior art in which use is made of the acoustic lens than in Embodiment 1, the range of sound field of narrow beam width is larger in Embodiment 1 than in the prior art.

Although the acoustic matching layer 7 of Embodiment 1 is a monolayer structure of an epoxy resin, similar effects can naturally be exerted by, for example, an acoustic matching layer 7 having a double layer structure composed of an epoxy resin layer and a layer of an epoxy resin containing alumina or the like as a filler or an acoustic matching layer 7 having a three layer structure including a polyethylene layer, a layer of an epoxy resin compounded with some filler and a machinable ceramics layer.

Figure 13:
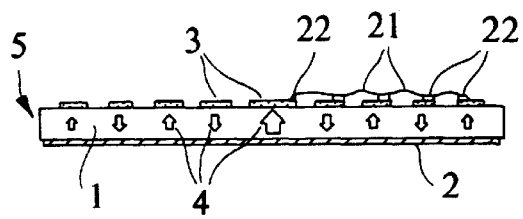
FIG. 13 is a view showing a modification of the electrode connection of the piezoelectric element according to Embodiment 1.

Although the split electrodes having the form of multi-rings are mutually connected by the use of a conductive resin in Embodiment 1, the connecting method is not particularly limited as long as the temperature is in the range in which the piezoelectric element 5 is not depoled. If electrical connection is attained, a conductive thin wire may be connected by means of solder 22 as shown in FIG. 13 or other methods such as thermocompression bonding may be effected to thereby induce similar performance.

Figure 14:
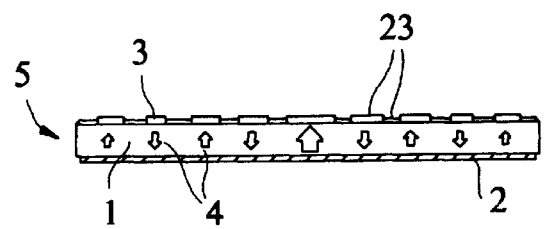
FIG. 14 is a view showing another modification of the electrode connection of the piezoelectric element according to Embodiment 1.

Instead of the connection on the piezoelectric ceramic 1, the electrical connection between the individual split electrodes may be effected by means of the acoustic backing layer 8 composed of a conductive material. In this instance, the acoustic backing layer 8 is used comprising an epoxy resin and, mixed therein in high concentration, metal thin wires or particles. The acoustic backing layer 8 is arranged on the side of the split electrodes 3. Further, as another modification, a metal film 23 may be provided on all the surface on the split electrode 3 side of the piezoelectric ceramic 1 by sputtering or a similar method as shown in FIG. 14. In this method, more secure electrical connection is achieved than in the method comprising linearly connecting the split electrodes 3, thereby enhancing the reliability.

Figure 15:
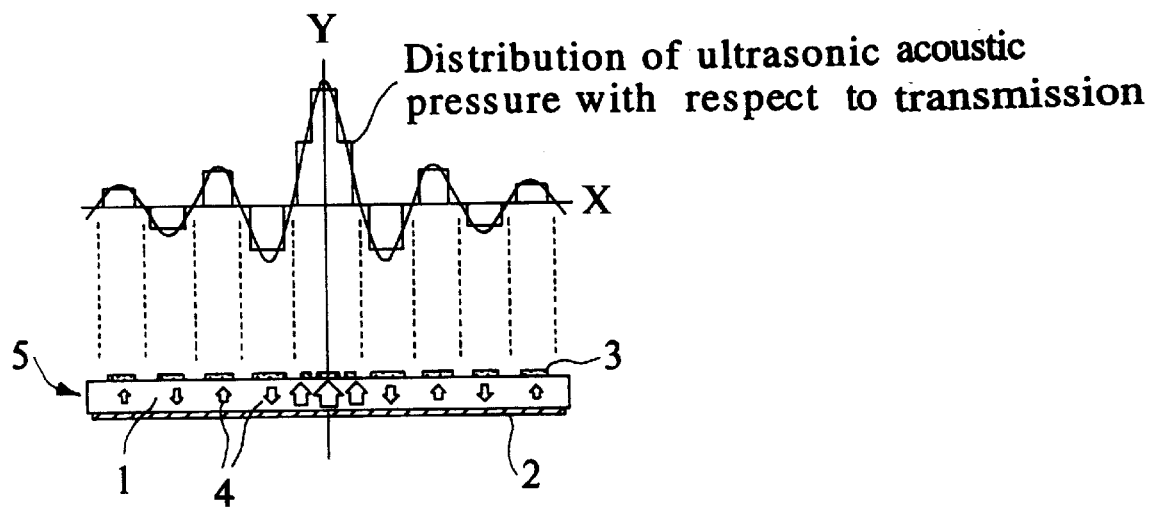
FIG. 15 is a view showing the Bessel function and the ultrasonic acoustic pressure distribution of the piezoelectric element according to Embodiment 1.

Referring to FIG. 15, one of the hills or valleys of the Bessel function may be divided into at least two parts and the intensities of spontaneous polarization may be varied between the respective split electrode 3 parts. This enables obtaining an acoustic pressure distribution more accurately having the form of Bessel function, so that the range ensuring line focus is enlarged.

Although the zeroth-order Bessel function having two positive (+)-side hills and two negative (-)-side valleys on each side excluding the center is employed in Embodiment 1, the nondiffracting beam can be realized as long as there exist at least one positive (+)-side hill and at least one negative (-)-side valley on each side excluding the center to thereby enable obtaining the same effects as in Embodiment 1. FIG. 5 is a view showing the positions of the split electrodes 3 of the piezoelectric element 5 having one positive (+)-side hill and one negative (-)-side valley on each side excluding the center together with their polarization directions and intensities 4.

However, the larger the number of such hills and valleys, the more accurate the approximation to the acoustic pressure distribution having the form of Bessel function, so that the distance in which the sound field propagates without diffusion as the nondiffracting beam is increased.

Moreover, although the polarization is conducted after the formation of electrodes in the form of multi-rings in Embodiment 1, the same effects can be exerted by conducting polarization while contacting an electrode composed of a conductor such as conductive rubber and an insulating material with the piezoelectric ceramic 1 without arranging an electrode on at least one side of the piezoelectric ceramic 1 and thereafter applying an electrode to all the surface by the method enabling film formation at a range of temperatures within which depolarization does not occur such as sputtering or vapor deposition.

Figure 16:
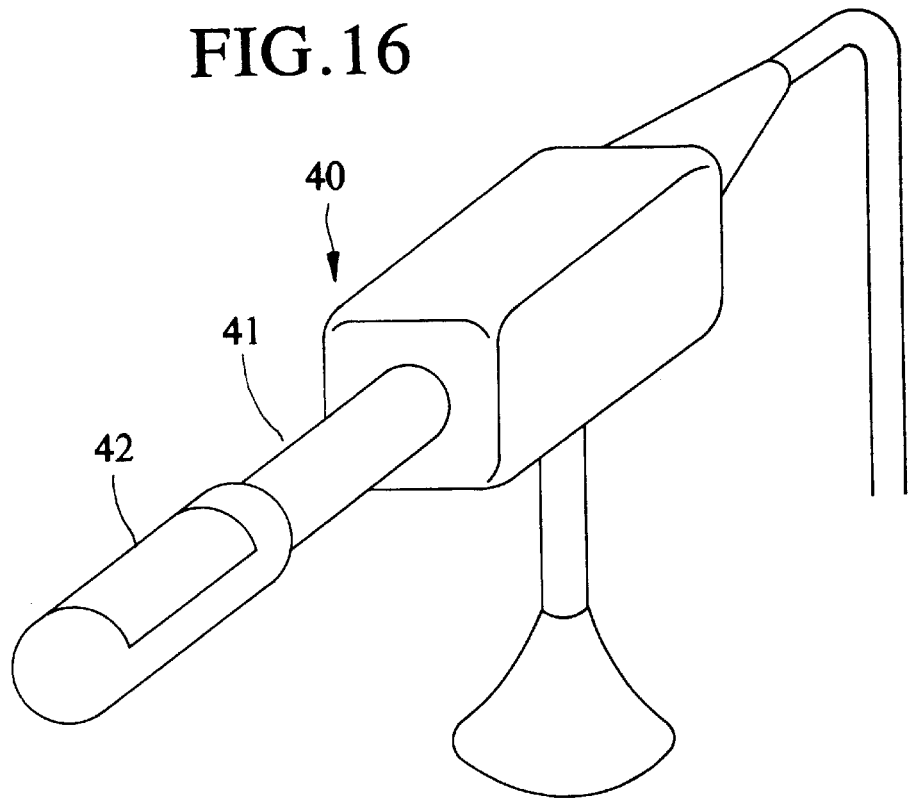
FIG. 16 is a view of the transrectal probe of Embodiment 1.
Figure 17:
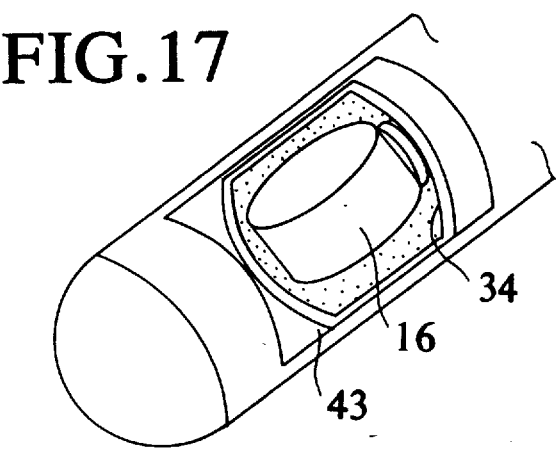
FIG. 17 is a partial enlarged view showing the transducer part assembled in the transrectal probe of Embodiment 1.

FIGS. 16 and 17 show an exemplary use of the transducer part 16 of Embodiment 1 in a transrectal probe device 40. Any optical diagnostic system is not provided for transrectal purposes, and the insertion part 41 is hard. The tip 42 has a diameter of about 25 mm and is provided with an acoustic window 43.

With respect to the transrectal probe device 40 shown in FIGS. 16 and 17, one of a relatively large size can be used, so that the transducer part 16 and the piezoelectric ceramic 1 can be of large size. Therefore, the number of hills and valleys of the Bessel function can be larger than in FIG. 2 to thereby enable transmitting ultrasonic beam with a Bessel acoustic pressure distribution of greater accuracy.

Consequently, the region in which the ultrasonic beam does not diffuse with the result that clear ultrasonic image can be obtained is enlarged. Also, the ultrasonic probe is suitable for use in the observation and diagnosis of not only the rectal wall but also the peripheral lymph node and peripheral organ such as prostate gland. Moreover, a therapeutic transducer not shown which can transmit strong continuous or burst ultrasonic wave is arranged in a probe device to thereby obtain a therapeutic probe device capable of ultrasonic therapy and ultrasonic diagnosis.

Figure 18:
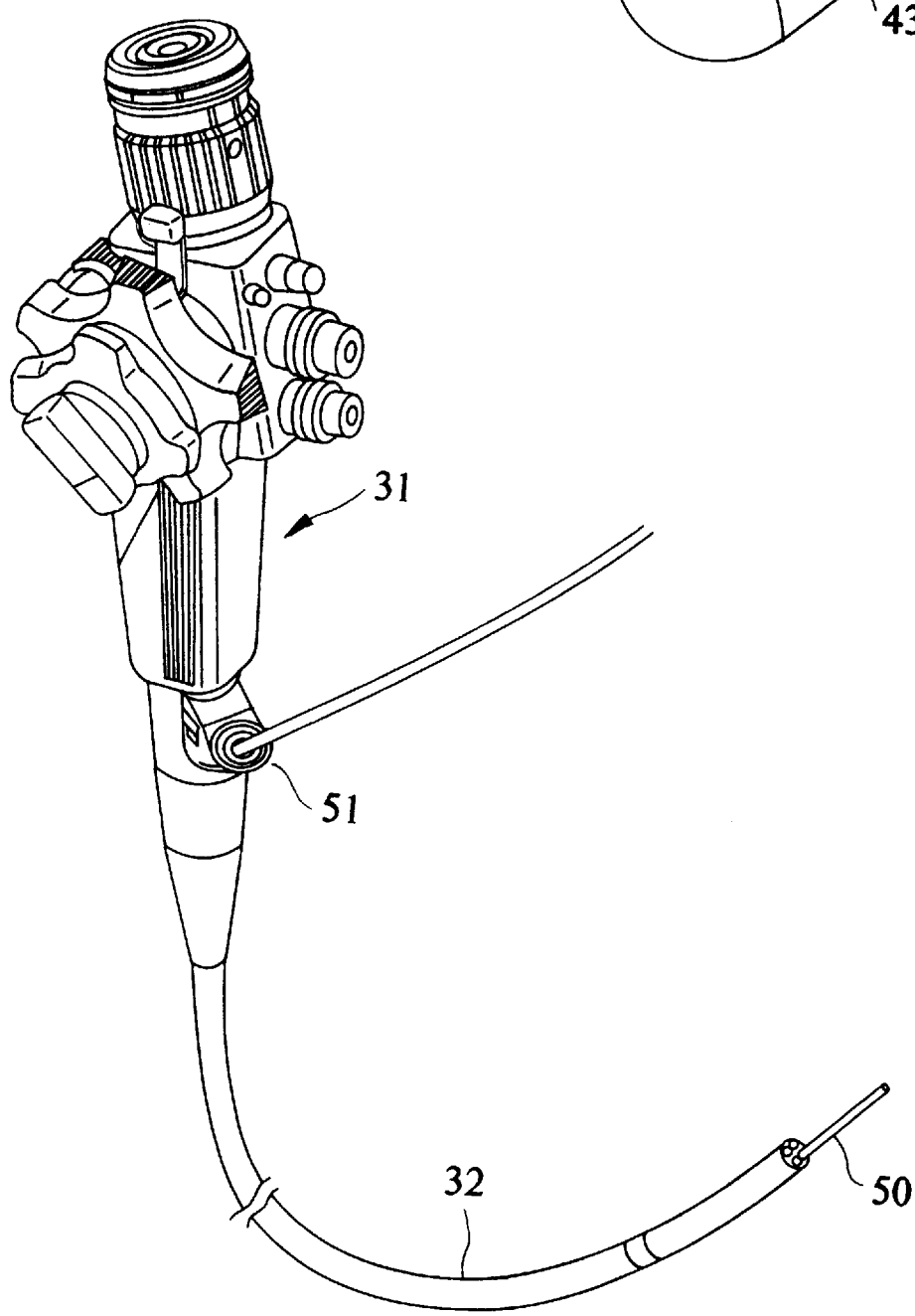
FIG. 18 is a view of the small-diameter probe for transforceps channel of Embodiment 1.
Figure 19:
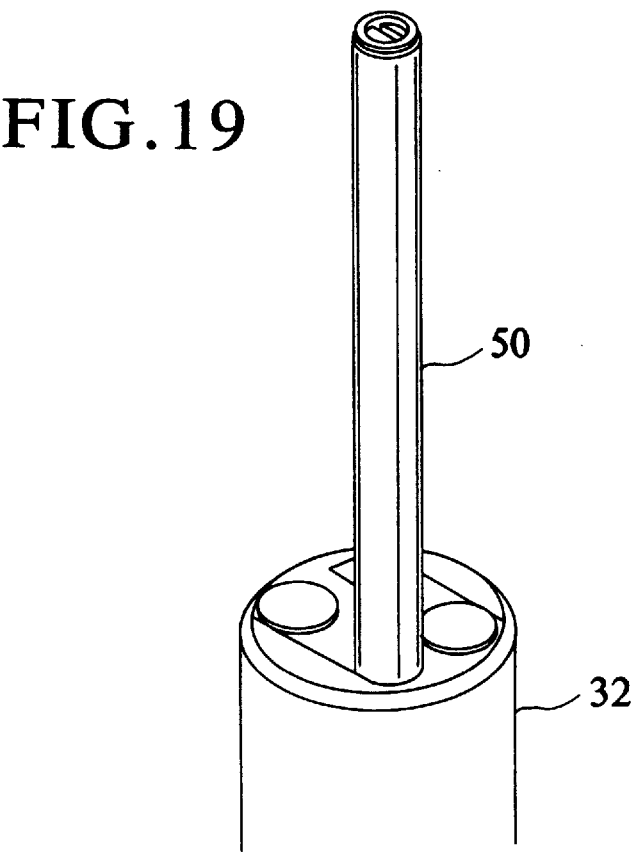
FIG. 19 is an enlarged view of the small-diameter probe for transforceps channel of Embodiment 1.
Figure 20:
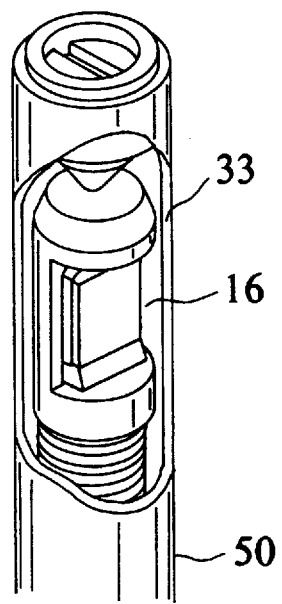
FIG. 20 is a partial enlarged view showing the transducer part assembled in the small-diameter probe for transforceps channel of Embodiment 1.

An example of use of the transducer part 16 of Embodiment 1 in a small-diameter probe device for transforceps channel 50 is shown in FIGS. 18 to 20. This is an ultrasonic probe device of about 2 mm in diameter which is thin and flexible, having no optical system. Referring to FIG. 18, the device is guided toward the target site by the forceps channel inlet of the conventional endoscope to thereby conduct ultrasonic diagnosis. In FIG. 18, the polarization intensity is nil outside the most peripheral circular polarized part which has been provided with the same concentric circular polarization distribution as in Embodiment 1 on the rectangular piezoelectric element.

The employment of the above transducer part 16 enables even the small-diameter probe device for transforceps channel 50 of small size and of low output to send ultrasonic beam to a distant place because of the reduced diffusion of the ultrasonic beam to thereby carry out observation and diagnosis.

Embodiment 2

Figure 21:
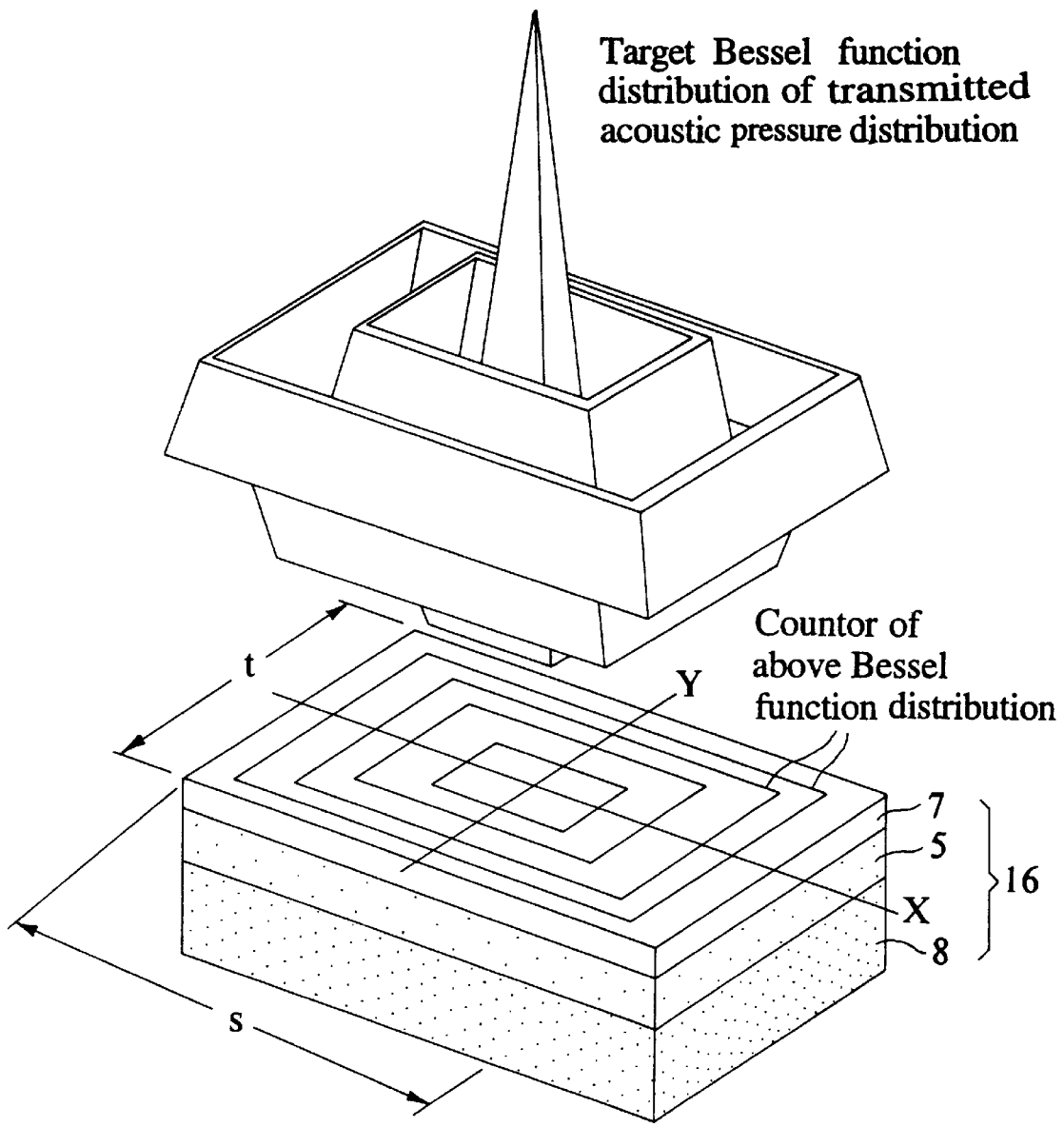
FIG. 21 is an explanatory view of the rectangular transducer part and transmitted acoustic pressure distribution according to Embodiment 2.

FIG. 21 shows Embodiment 2 of the present invention. In Embodiment 2, the invention is applied to a rectangular piezoelectric element 5. The piezoelectric element has its intensity of spontaneous polarization determined as follows:

provided that the rectangle has two sides each having a length of s and two sides each having a length of t, that the rectangle has its center, i.e., intersection of diagonal lines agreeing with the origin of the X-Y coordinate system and that two sides of the rectangle are parallel to the X-axis while the other two sides are parallel to the Y-axis, the intensity of spontaneous polarization is determined so that an acoustic pressure is transmitted being proportional to $J_0$ (X*s*a) when point (X, Y) is present within a triangle including the origin and consisting of lines each having a length of s and $J_0$ (Y*t*a) when point (X, Y) is present within a triangle including the origin and consisting of lines each having a length of t, namely, having a contour of similar square morphologies with identical geometric centers.

A transducer part 16 is fabricated with the use of the piezoelectric element having the thus determined spontaneous polarization distribution in the same manner as in Embodiment 1 and used in, for example, an ultrasonic endoscope.

Figure 22:
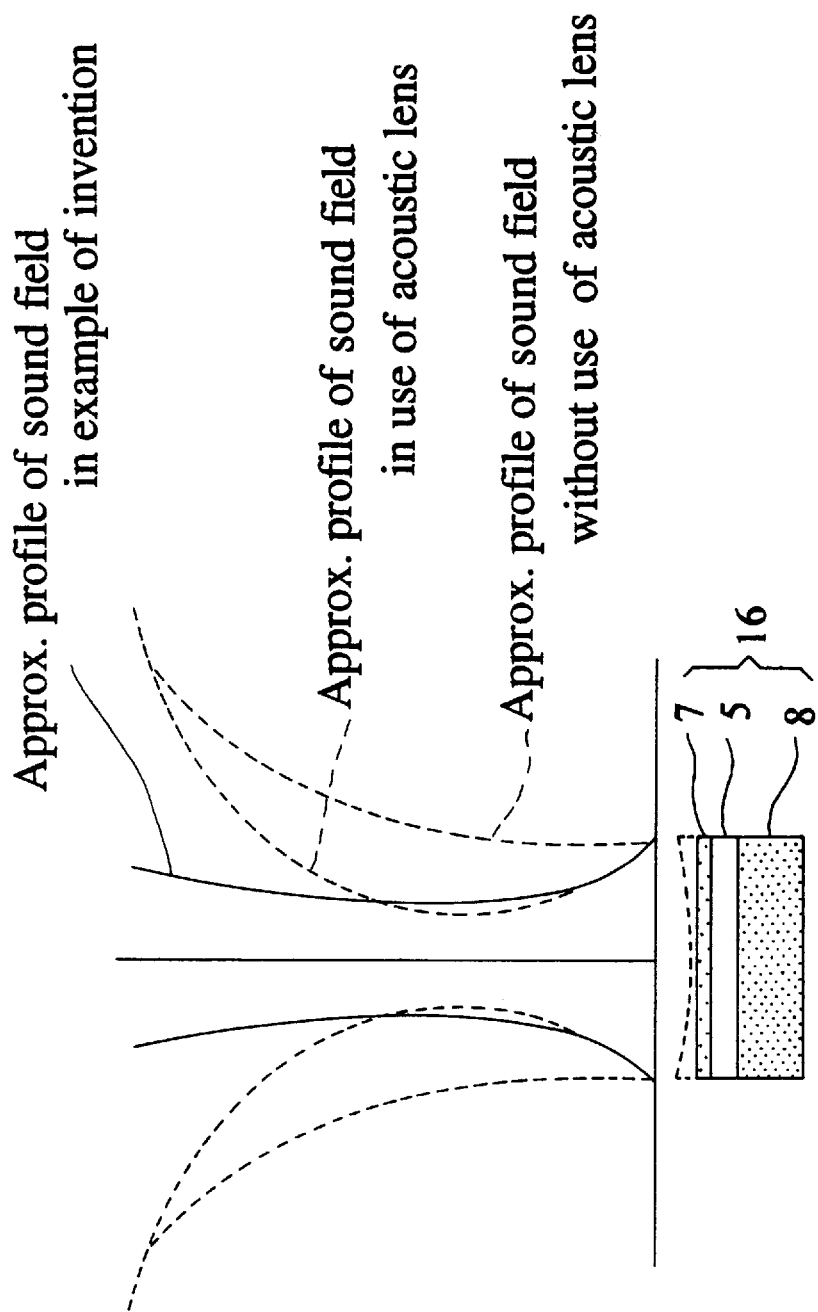
FIG. 22 is a schematic diagram showing sound field profiles according to Embodiment 2 and the prior art.

Referring to FIG. 22, this transducer part 16 enables obtaining a nondiffracting sound field having the acoustic pressure distributed in the form of Bessel function at each section of the ultrasonic beam as shown in FIG. 12, which does not diffuse by propagation.

In Embodiment 2, a thinner insertion part 32 for use in, for example, an ultrasonic endoscope can be realized while retaining the same ultrasonic wave transmitting area as in the circular ultrasonic transducer. This is effective in improving the insertability and alleviating the pain of the examinee. In particular, the use thereof in the ultrasonic probe device of small diameter as shown in FIG. 18 is advantageous.

Embodiment 3

Figure 23:
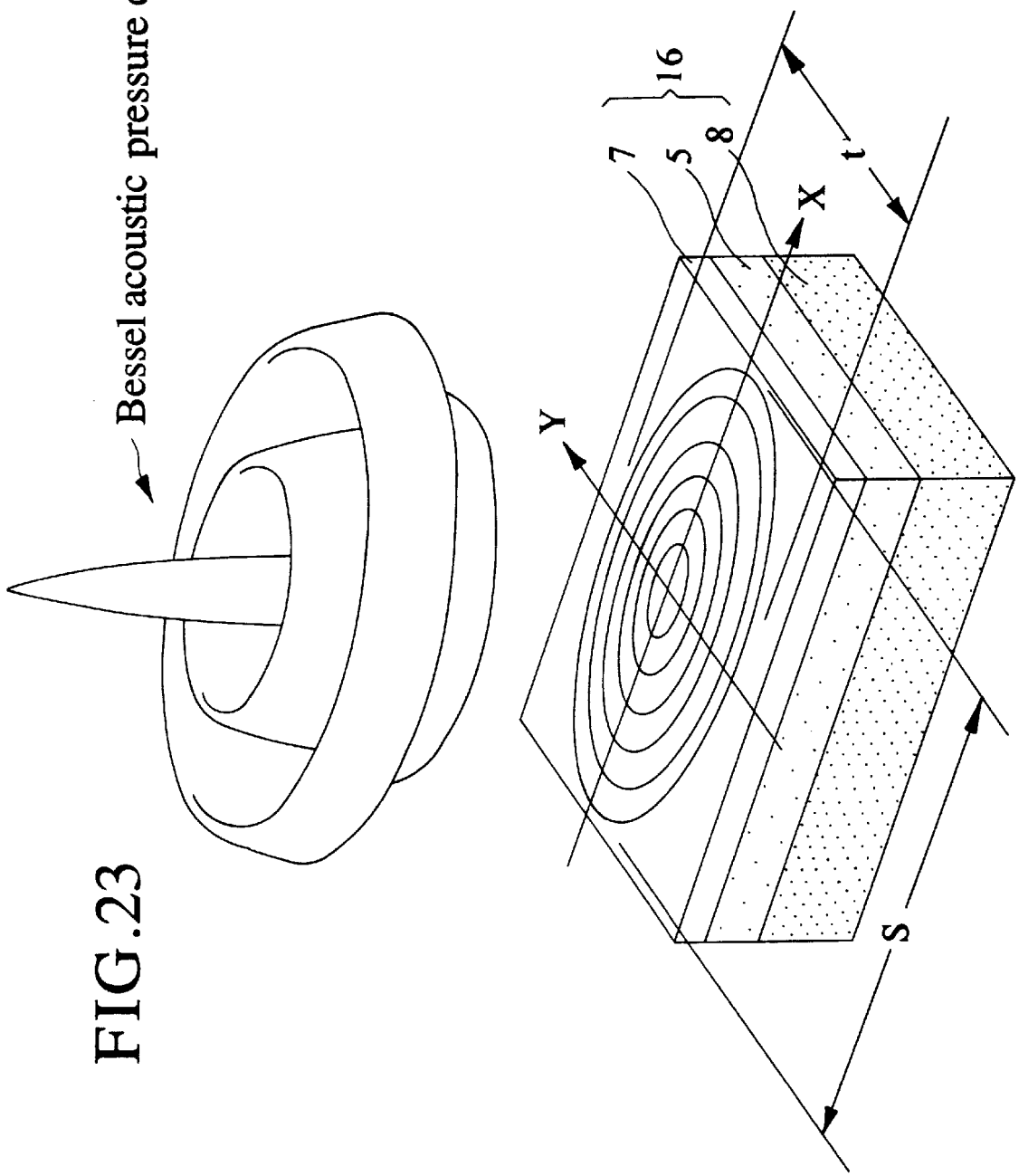
FIG. 23 is an explanatory view of the rectangular transducer part and transmitted acoustic pressure distribution according to Embodiment 3.

FIG. 23 shows the transducer part 16 provided with an elliptic polarization intensity distribution according to Embodiment 3. The piezoelectric element has its intensity of spontaneous polarization determined as follows:

provided that the ellipse has a major axis having a length of s and a minor axis having a length of t, that the ellipse has its center, i.e., middle point of two focuses agreeing with the origin of the X-Y coordinate system and that the major axis and the minor axis of the ellipse are caused to agree with the X-axis and the Y-axis, respectively, the distribution of spontaneous polarization is determined so that an acoustic pressure with a profile obtained by enlarging the Bessel distribution of the circular piezoelectric element (shown in FIG. 2 according to Embodiment 1) by a factor of s/t in the direction of the Y-axis is transmitted.

In Embodiment 3, referring to FIG. 23, the acoustic pressure is distributed in the form of Bessel function at each section of the ultrasonic beam, so that the use of the transducer part 16 structured according to Embodiment 3 also enables obtaining a nondiffracting sound field which does not diffuse by propagation.

That is, a thinner insertion part 32 for use in, for example, an ultrasonic endoscope can be realized while retaining the same ultrasonic wave transmitting area as in the circular transducer part 16. This is effective in improving the insertability and alleviating the pain of the examinee. Further, as different from Embodiment 2, there is no corner in the spontaneous polarization distribution and the relevant transmitted acoustic pressure distribution, so that the piezoelectric element is free of the disorder of sound field attributed to edge. This enables maintaining the Bessel nondiffracting sound field over an extended range to thereby realize propagation of ultrasonic wave without diffusion, so that clear ultrasonic image can be obtained.

Although the piezoelectric element 5 has a rectangular shape in FIG. 23, the same effects can be exerted by the use of the piezoelectric element 5 itself having an elliptic shape.

Embodiment 4

Figure 25:
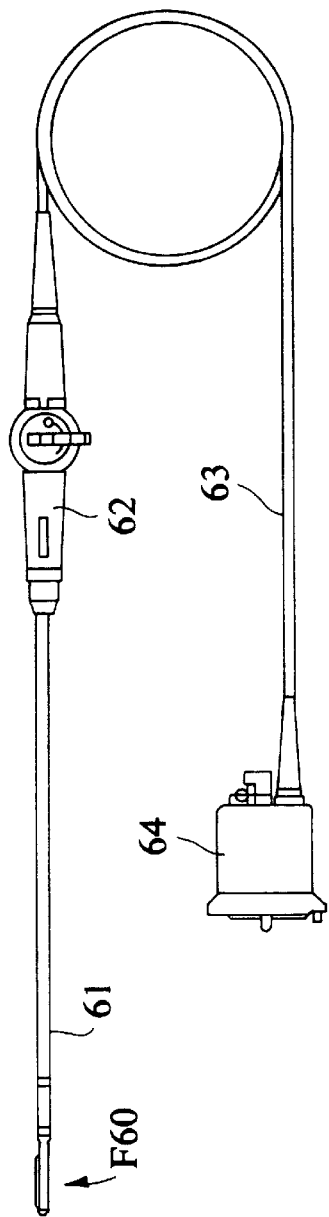
FIG. 25 is a view showing the ultrasonic endoscope including the ultrasonic laparoprobe according to Embodiment 4.
Figure 26:
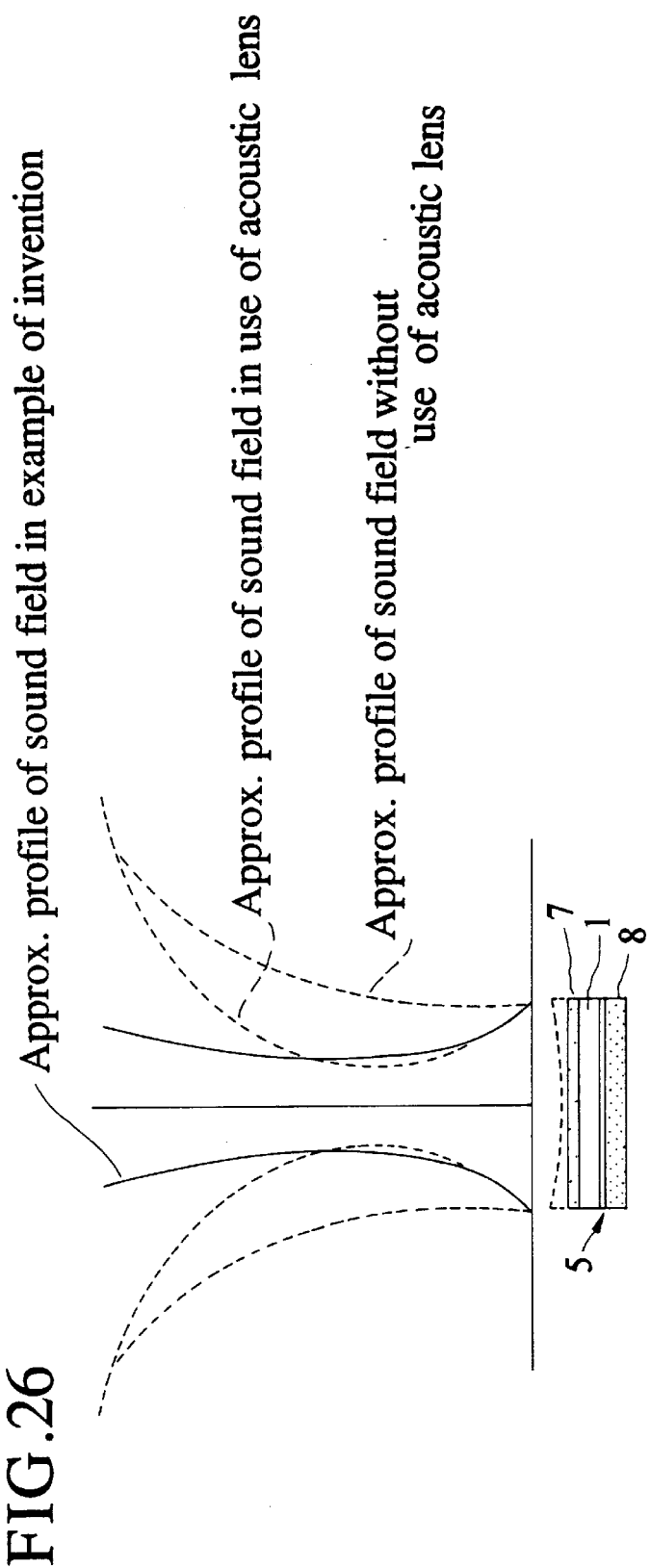
FIG. 26 is a schematic diagram showing sound field profiles of the piezoelectric element of Embodiment 4 and the prior art.

An exemplary use of the ultrasonic probe of the linear array type structured according to the present invention 60 in an ultrasonic laparoprobe device will be described with reference to FIGS. 24 to 26. The ultrasonic laparoprobe device has the ultrasonic probe arranged in the tip of a hard insertion part 61.

The insertion part 61 is provided at its rear end with a holding part 62 to be held by the operator. The holding part 62 is connected through a cord 63 to a connector 64. The connector 64 can be connected to an ultrasonic diagnostic equipment not shown.

The fundamental structure of the ultrasonic probe of the linear array type 60 is the same as that of the conventional one, so that only an outline thereof will be described. The ultrasonic probe of the linear array type 60 comprises a row of horizontally arranged small elements each composed of a small rectangular piezoelectric ceramic 1 and, connected to each small element, a cable for application of energizing pulse voltage and for receiving and transmission of signals which is not shown.

An acoustic matching layer 7 and an acoustic backing layer 8 are disposed on the outer face and the back of each piezoelectric ceramic 1, respectively.

Figure 24:
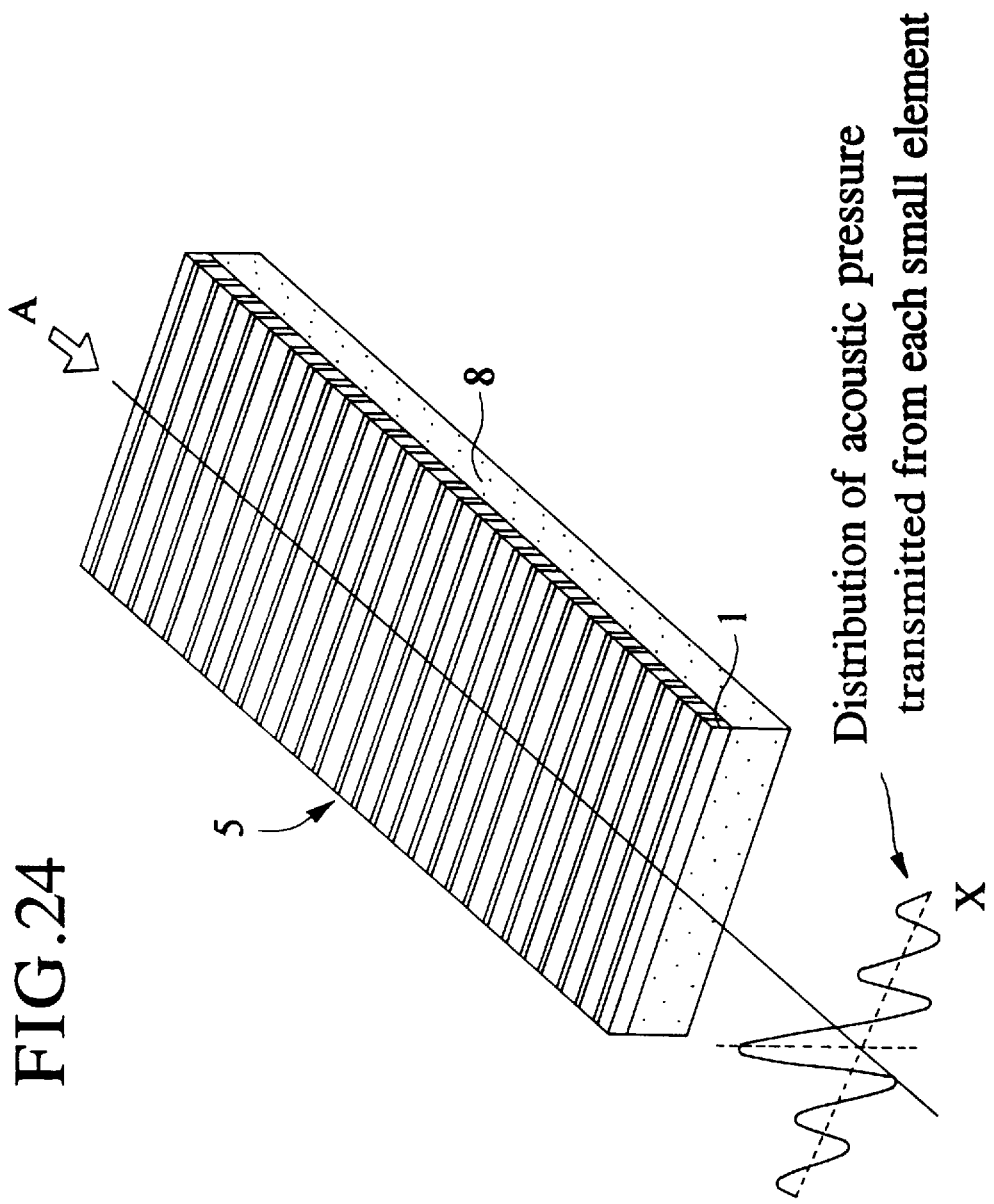
FIG. 24 is a perspective view of the piezoelectric element of Embodiment 4.

Referring to FIG. 24, each small element of the piezoelectric element 5 is polarized so as to transmit the sound field of the Bessel function. In particular, the spontaneous polarization distribution is provided so that, provided that the Bessel function of $J_0$ (x/a) (wherein a is a constant) is set on an axis parallel to a long side of each small element with the assumption of X-axis of coordinate having its origin at an middle point of the above long side, the acoustic pressure is distributed in a profile resulting from parallel movement of the Bessel function along a short side of the small element. The individual small elements of the piezoelectric element 5 are linearly arranged in the direction of the minor axes of the small elements.

The direction in which the small elements are lined up agrees with the major axis direction of the ultrasonic probe.

In the major axis direction of the ultrasonic probe 60, the position of the focus is controlled by the conventional electronic focusing technique to thereby effect a control such that clear image is obtained at appropriate position.

On the other hand, in the direction of the minor axis of the ultrasonic probe, the ultrasonic wave with the acoustic pressure distribution of the Bessel function is transmitted by virtue of the spontaneous polarization distribution of the piezoelectric element 5, so that the nondiffracting sound field is formed. As for the conventional electronic scanning linear array ultrasonic probe, the position of the focus of the ultrasonic beam has been controlled by electronic focusing in the major axis direction, i.e., scanning face direction of the ultrasonic probe to thereby enable clearly extracting needed site.

Figure 28:
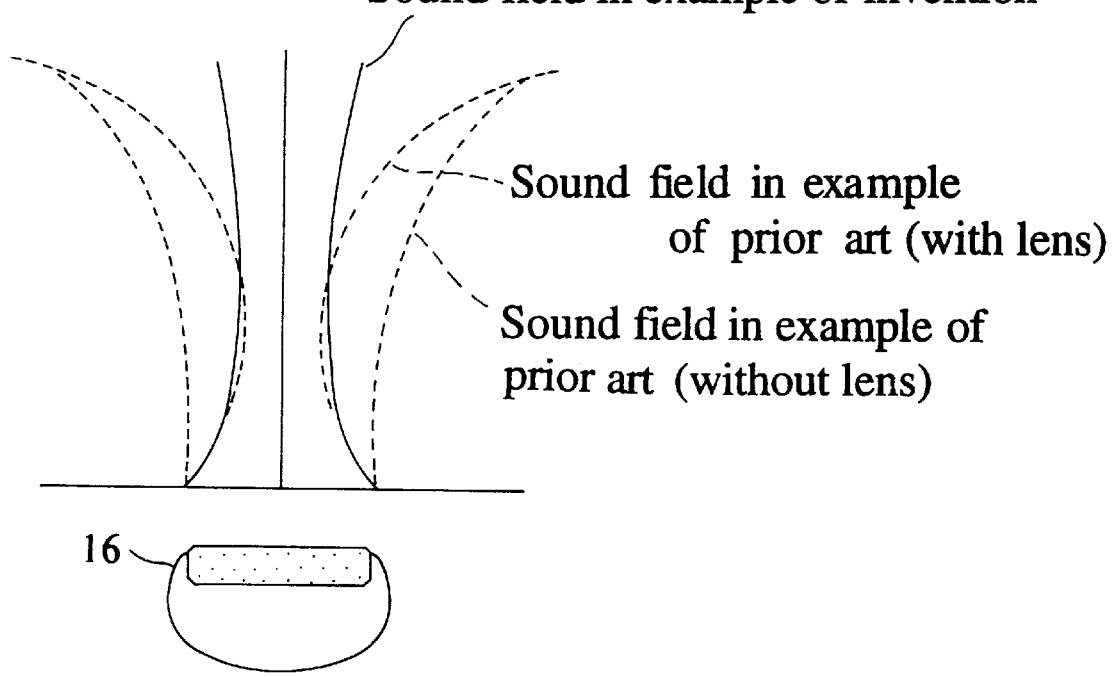
FIG. 28 is a schematic diagram showing sound field profiles of the piezoelectric element of Embodiment 4 and the prior art.

However, the ultrasonic beam has been controlled only by the acoustic lens mounted on the piezoelectric element 5 in the direction of the minor axis, i.e., the direction of the scanning face thickness of the ultrasonic probe. Consequently, although the ultrasonic beam becomes slender so as to enable obtaining clear image around the focus of the acoustic lens as shown in FIG. 28, the ultrasonic beam has been expanded so as to make image obscure at other positions. In contrast, the constitution of Embodiment 4 enables obtaining the ultrasonic beam with the width substantially uniform in the direction of the scanning plane thickness as shown in FIG. 28, so that clear image can be obtained all over the ultrasonic image. Especially, it is highly effective in the extraction of distant zone in which the diffusion of the ultrasonic beam is inevitable in the use of the conventional acoustic lens system.

Modification 1 to Embodiment 4

The piezoelectric element 5 may have a square shape in Embodiment 4.

Modification 2 to Embodiment 4

Figure 27:
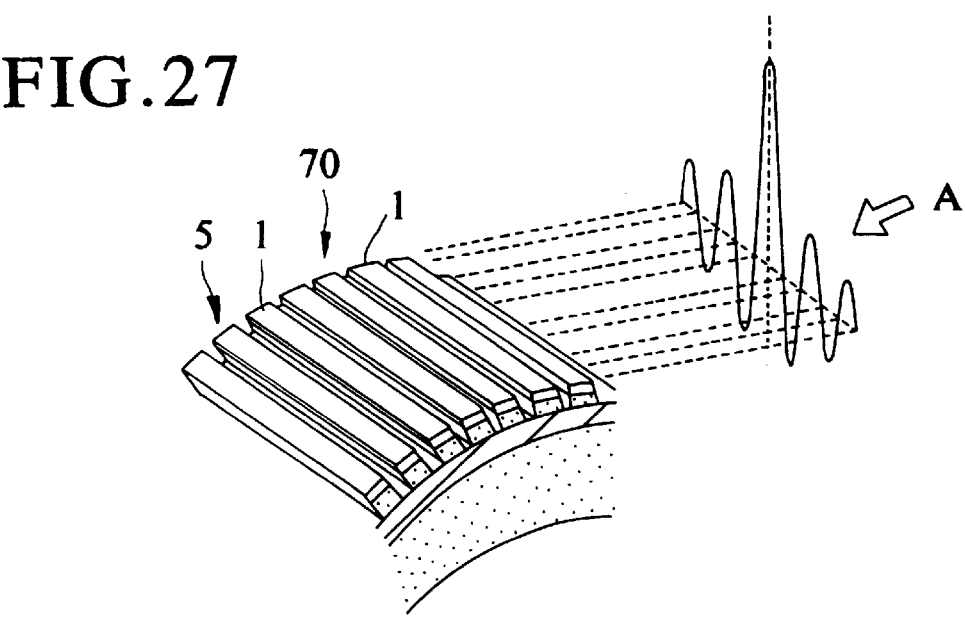
FIG. 27 is a schematic diagram showing the electronic convex scanning ultrasonic probe of Embodiment 4.

Embodiment 4 is applicable to not only the electronic linear scanning ultrasonic probe device but also the electronic convex scanning ultrasonic probe device 70 as shown in FIG. 27.

Figure 29:
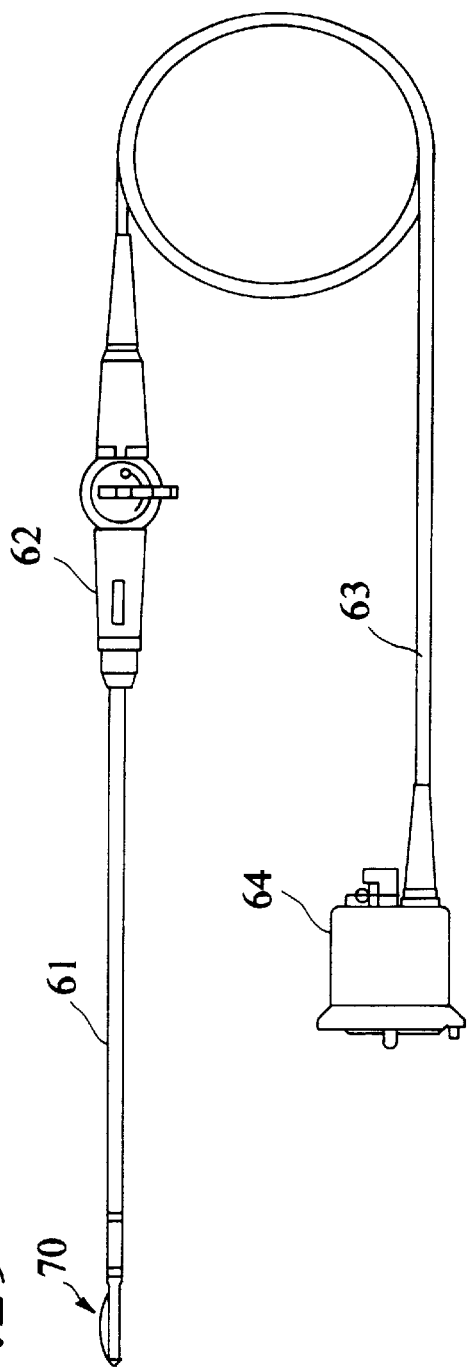
FIG. 29 is a view showing the endoscope including the electronic convex scanning ultrasonic probe.

In the endoscope of FIG. 29 including the electronic convex scanning ultrasonic probe device of FIG. 27, the piezoelectric element 5 is structured by piezoelectric ceramics 1 which have fundamentally the same feature as in FIG. 24 according to Embodiment 4 but which are arranged in a shape curved in convex form.

In this modification, the timing of energizing pulse voltage application is selected in conformity to the configuration of the surface of the ultrasonic probe device 70 so that the transmitted ultrasonic wave front is in a plane perpendicular to the acoustic axis.

In Embodiment 4, the use of the technology of the present invention in a convex scanning ultrasonic probe with a broad angle of view enables clear extraction of wider application site.

Modification 3 to Embodiment 4

Figure 31:
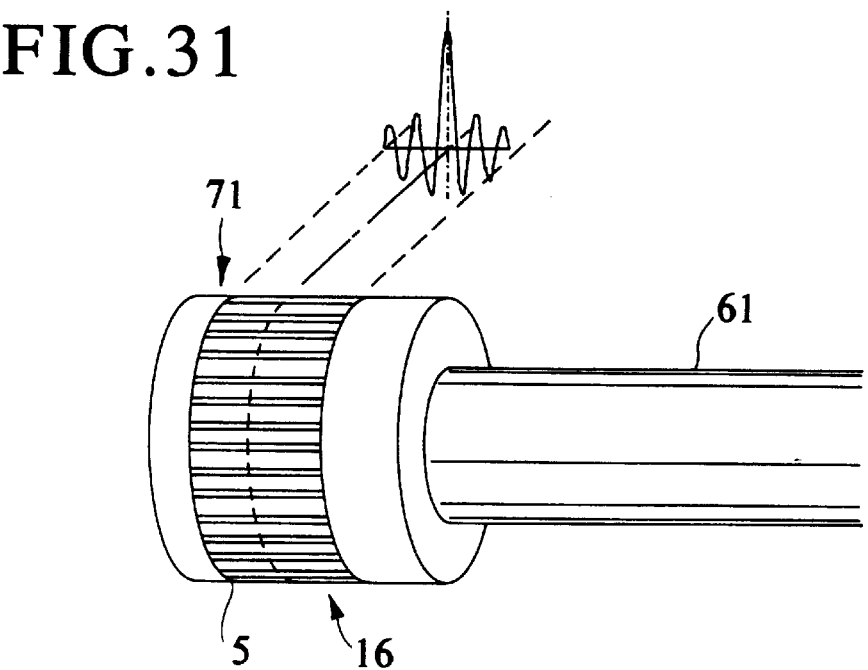
FIG. 31 is an enlarged view of the electronic scanning ultrasonic probe.
Figure 32:
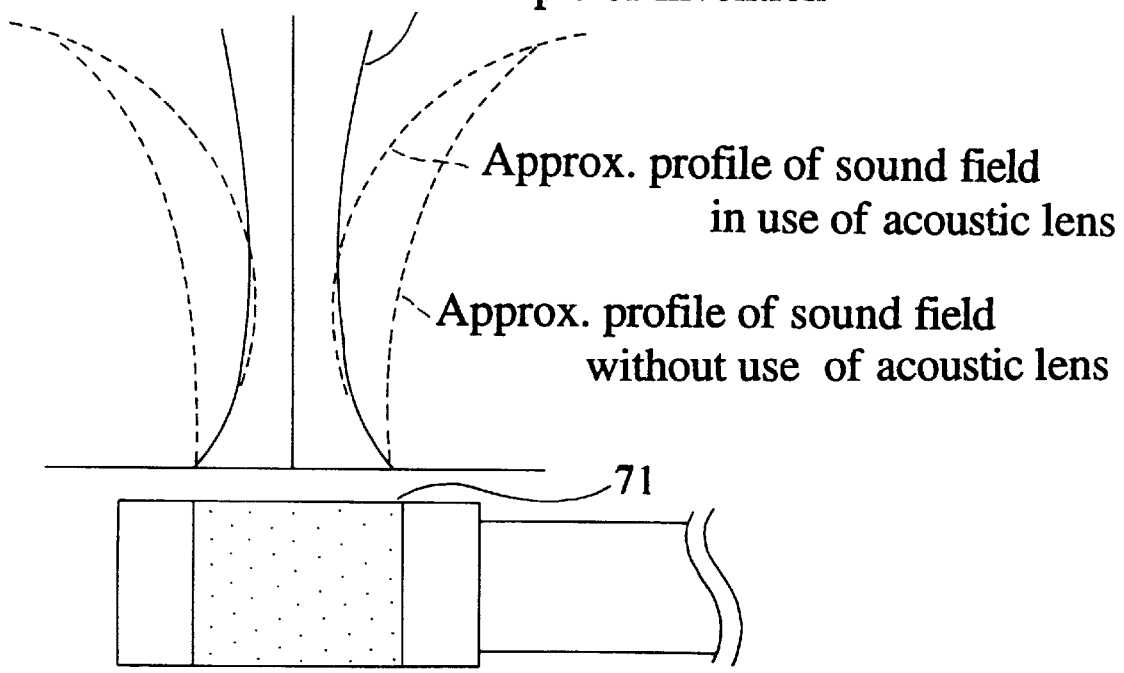
FIG. 32 is a schematic diagram showing sound field profiles according to Embodiment 4 and the prior art.

Embodiment 4 is applicable to not only the electronic linear scanning ultrasonic probe device but also the electronic radial scanning ultrasonic probe device 71 as shown in FIG. 31.

Figure 30:
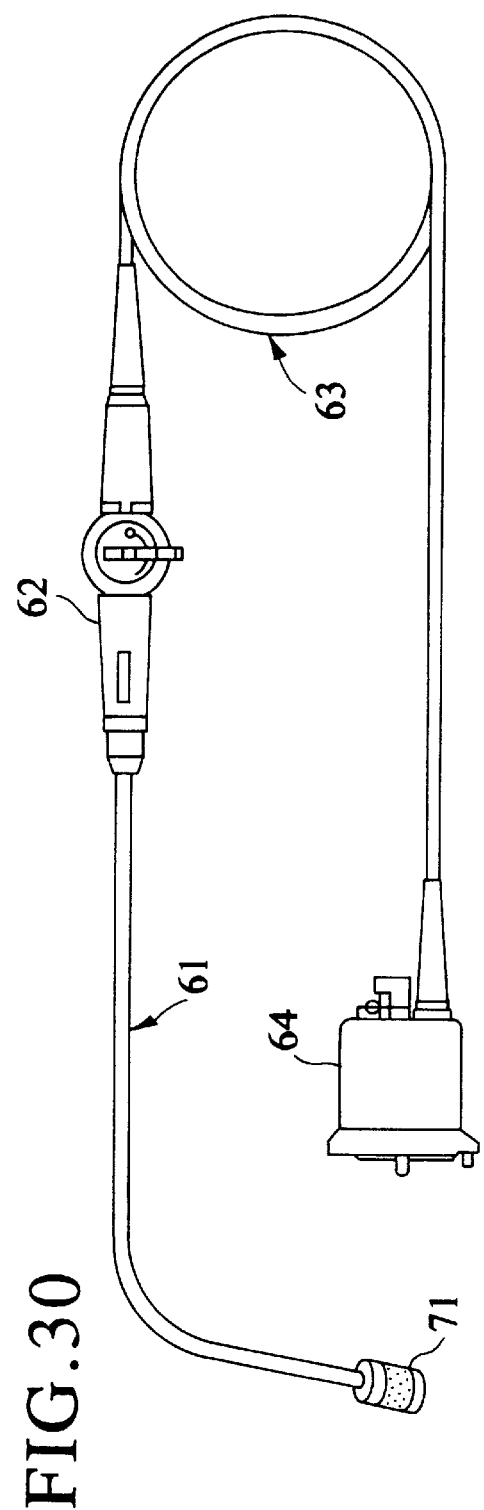
FIG. 30 is a view showing the endoscope including the electronic scanning ultrasonic probe.

In the electronic convex scanning ultrasonic endoscope of FIG. 30, the piezoelectric element 5 having fundamentally the same structure as in Embodiment 4 is arranged in a shape curved in convex form as shown in FIG. 31.

In this modification, the timing of energizing pulse voltage application is selected in conformity to the configuration of the surface of the ultrasonic probe device 71 so that the transmitted ultrasonic wave front is in a plane perpendicular to the acoustic axis.

In Embodiment 4, the use of the technology of the present invention in the electronic radial scanning ultrasonic probe device 71 advantageously employed in conducting scanning from inside a pipe cavity enables clear extraction of wider application site.

In the radial scanning, the acoustic beam spacing is increased and the ultrasonic wave is attenuated as the distance is increased. However, the diffusion of the ultrasonic beam is little in the use of the transducer part 16 structured according to Embodiment 4, so that, even if the small-diameter probe device of small size and of low output is employed, the ultrasonic wave can be sent to a distant place to thereby carry out observation and diagnosis. Conventional one can be used as the ultrasonic diagnostic equipment in which the above electronic radial scanning ultrasonic probe device is assembled.

Embodiment 5

Figure 33:
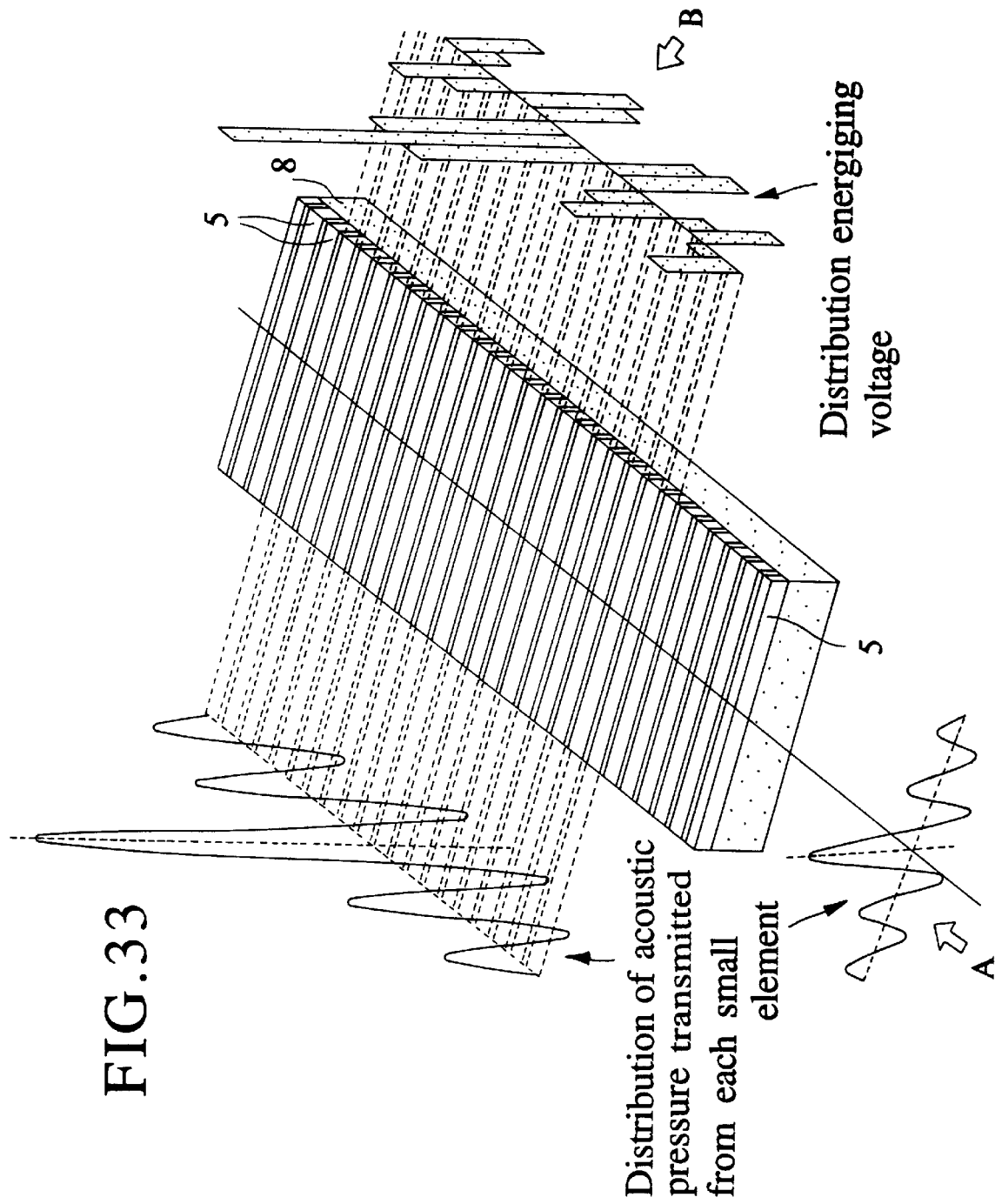
FIG. 33 is a view showing the piezoelectric element, energizing pulse voltage and sound field according to Embodiment 5.
Figure 34:
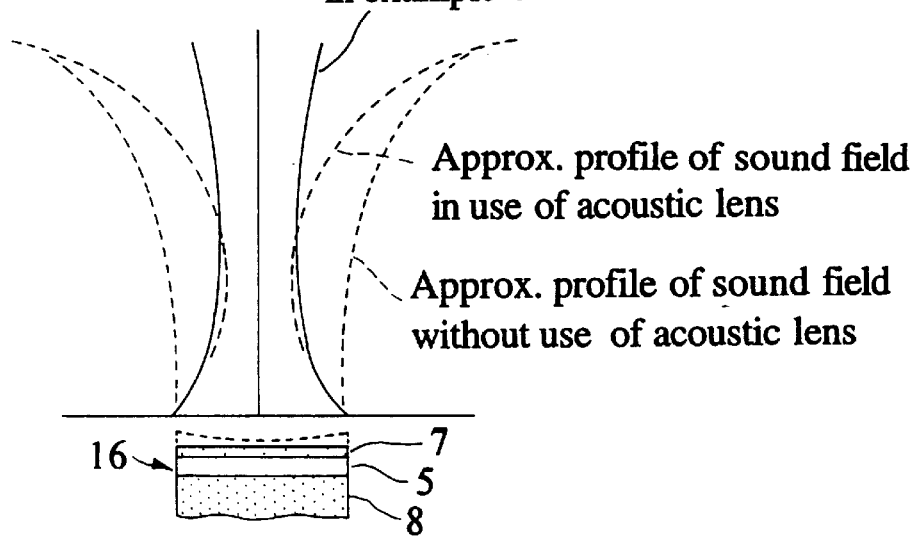
FIG. 34 is a schematic diagram of sound field viewed from the A-side of FIG. 33.
Figure 35:
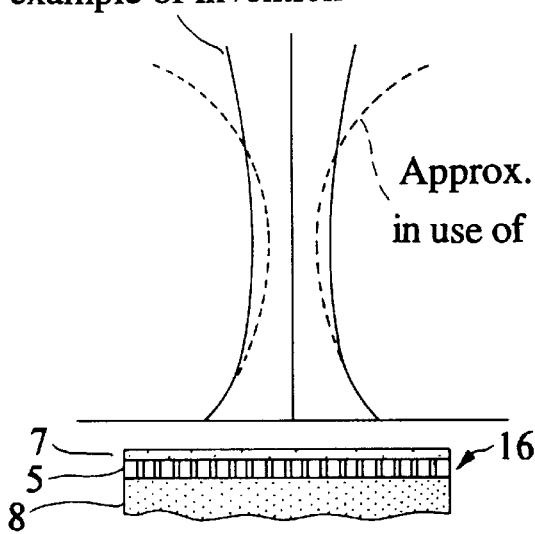
FIG. 35 is a schematic diagram of sound field viewed from the B-side of FIG. 33.

Embodiment 5 of the present invention is as shown in FIGS. 33 to 35. The structure of each part of the ultrasonic probe is the same as in Embodiment 4.

The methods of driving the piezoelectric element 5 are different between Embodiment 5 and Embodiment 4. In Embodiment 4, the position of the focus is controlled by the deviation in driving timing of each small element of the piezoelectric element 5 with the use of the conventional electronic focusing technique.

In Embodiment 5, the driving timings of the individual small elements are rendered identical with each other and the polarity and magnitude of each energizing pulse are determined on the basis of the zeroth-order Bessel function. The polarity and magnitude of each energizing pulse are determined in the following manner.

Provided that a row of small elements employed for forming a single acoustic beam are designated as one block, that the direction in which the small elements are lined up is defined as Y-axis with the geometric center of each block designated as the origin of the Y-axis and that the zeroth-order Bessel function of $J_0$ (y/b) wherein b is a constant is assumed along the Y-axis, values of the zeroth-order Bessel function are averaged every small-element length in the same manner as shown in FIG. 3, the average value being designated as a target acoustic pressure to be transmitted by each small element, and energizing pulse voltage and its polarity are controlled so as to transmit the above target acoustic pressure with the use of the facts that driving of the piezoelectric ceramic 1 of the piezoelectric element 5 at a high voltage leads to transmission of a high acoustic pressure while driving thereof at a low voltage leads to transmission of a low acoustic pressure and that conversion of the polarity of the energizing pulse causes the transmitted acoustic pressure to have a conversed phase.

In the above Embodiment 4, the conventional electronic focusing is employed in the direction of arrangement of the small elements. Thus, the ultrasonic beam is expanded at other than the focus position as shown in FIG. 35. FIG. 34 shows approximate sound field profiles viewed from the A-side of FIG. 33 as in the above FIG. 28, and FIG. 35 shows approximate sound field profiles viewed from the B-side of FIG. 33.

In the structure of Embodiment 5, the Bessel nondiffracting ultrasonic beam is obtained in the direction of arrangement of the small elements as well. Therefore, image clear in its entirety can be obtained by transmission and receiving of ultrasonic wave conducted once per acoustic beam, so that the frame rate can be enhanced.

Modification 1 to Embodiment 5

In this modification, use is made of the ultrasonic probe of Embodiment 5 having values of constants a, b determined so as to satisfy the relationship b=ta/s wherein s represents the width of element of one block (length of small element) and t represents the length of one block.

In the driving of one block of this ultrasonic probe device, the numbers of hills and valleys of the Bessel function are identical between the direction of arrangement of the small elements and the direction of scanning face thickness. Consequently, the acoustic pressure is distributed in the form of the Bessel function in any arbitrary section of the ultrasonic beam including the acoustic axis. Therefore, highly accurate nondiffracting ultrasonic beam can be transmitted.

Ultrasonic beam with the width substantially uniform in the direction of the scanning face thickness can be obtained as shown in FIG. 35, so that clear image can be obtained all over the ultrasonic image.

Embodiment 5 can be applied to the ultrasonic probe device having a flexible insertion part 61. Further, the application thereof is not limited to the above laparoprobe device and can be made to ultrasonic abdominal diagnosis from outside the body and to an ultrasonic endoscope for intraextremity scanning.

Modification 2 to Embodiment 5

Embodiment 5 is applicable to not only the electronic linear scanning ultrasonic probe device but also the electronic convex scanning ultrasonic probe device. The use of the technology of Embodiment 5 in a convex scanning ultrasonic probe with a broad angle of view enables clear extraction of wider application site.

Modification 3 to Embodiment 5

Embodiment 5 is applicable to not only the electronic linear scanning ultrasonic probe device but also the electronic radial scanning ultrasonic probe device. The use of the technology of the present invention in the radial scanning ultrasonic probe device advantageously employed in conducting scanning from inside a pipe cavity enables clear extraction of wider application site. In the radial scanning, the acoustic beam spacing is increased and the ultrasonic wave is attenuated as the distance is increased. However, the diffusion of the ultrasonic beam is little in the use of the transducer part 16 structured according to Embodiment 5, so that, even if the small-diameter probe device of small size and of low output is employed, the ultrasonic wave can be sent to a distant place to thereby carry out observation and diagnosis.

Embodiment 6

Figure 36:
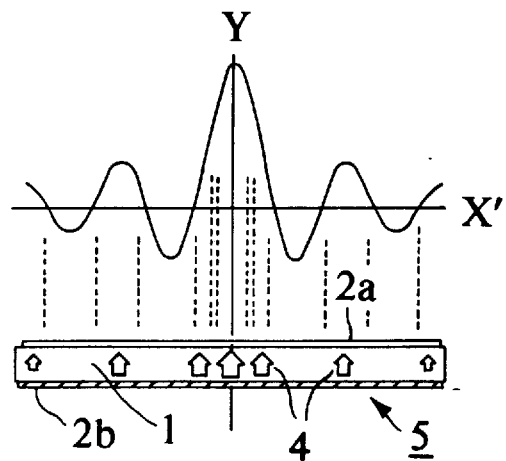
FIG. 36 is a view showing the Bessel function and piezoelectric element according to Embodiment 6.
Figure 37:
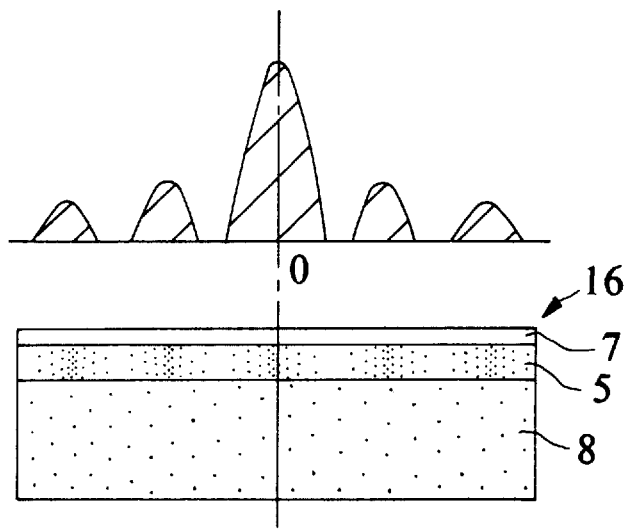
FIG. 37 is a view showing the transducer part and ultrasonic distribution according to Embodiment 6.
Figure 38:
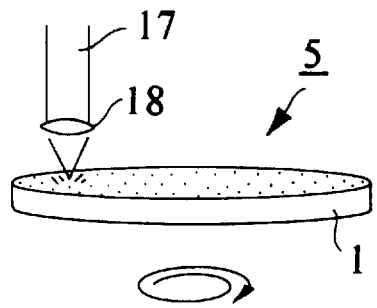
FIG. 38 is a schematic diagram showing the method of depolarizing the piezoelectric element according to Embodiment 6.
Figure 39:
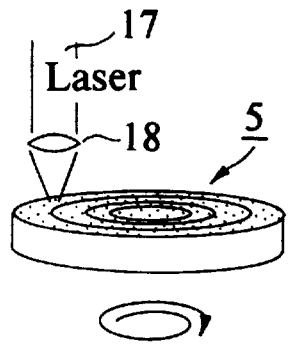
FIG. 39 is a schematic diagram showing the method of depolarizing the piezoelectric element according to Embodiment 6.
Figure 40:
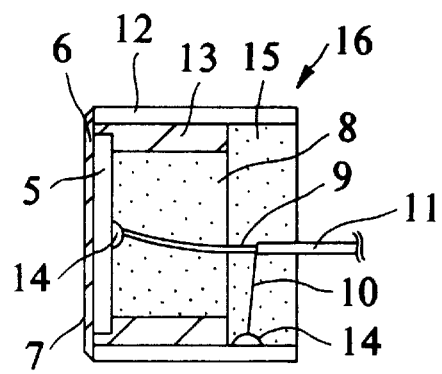
FIG. 40 is a sectional view of the transducer part according to Embodiment 6.

Embodiment 6 will be described with reference to FIGS. 36 to 40. FIG. 36 is a view showing the correlation between a section of the piezoelectric element 5 fabricated in Embodiment 6 and the Bessel function. FIG. 37 is a view showing the relationship between a section of the transducer part 16 as the ultrasonic probe including the piezoelectric element 5 fabricated in Embodiment 6 and the transmitted ultrasonic wave intensity distribution. FIGS. 38 and 39 are perspective views diagrammatically showing the method of depolarizing the piezoelectric element 5. FIG. 40 is a sectional view of the transducer part 16 including the piezoelectric element 5 fabricated in Embodiment 6.

The piezoelectric element 5 for use in the ultrasonic probe of Embodiment 6 and the process for producing the same will be described below. First, a lapped base of 10 mm in diameter and 160 $\mu$m in thickness composed of a PZT material is provided as the piezoelectric ceramic 1. Electrode paste (Ag/Pd) is applied to both principal surfaces of this base and baked. After the baking, the piezoelectric element 5 is polarized by the customary procedure to thereby obtain the uniformly polarized piezoelectric element 5.

This piezoelectric element 5 is adsorbed and fixed onto a jig equipped with a rotating means not shown. While being rotated, the piezoelectric element 5 is partially irradiated with YAG (yttrium aluminum garnet) laser beam 17 through a lens 18 and heated as shown in FIG. 38 to thereby effect partial depolarization. The laser beam (17) intensity, condensing ratio, irradiation time, ambient temperature, etc. are regulated and the temperature of the light receiving part is controlled to thereby vary the degree of depolarization, so that differences are created in the degree of polarization (shown by density differences between a multiplicity of points) as on the piezoelectric element 5 of the transducer part 16 shown in lower part of FIG. 37. That is, in FIG. 37, the deeper the color of each part of the piezoelectric element 5, the less the depolarization at the part. The white indicates that the part is a zone where the depolarization is complete so that the piezoelectricity has been lost. In Embodiment 6, the depolarization has been attained by the method in which the piezoelectric element 5 is adsorbed and fixed onto a jig equipped with a rotating means not shown and in which, while rotating the piezoelectric element 5, the full covering electrode 2 is partially irradiated with YAG laser beam 17 through a lens 18 and heated.

In Embodiment 6, the atmosphere has been regulated by blowing nitrogen gas of about 0° C. onto the piezoelectric element 5 so as to prevent the temperature from rising at other than in the vicinity of the zone irradiated with laser beam 17. The distribution of polarization intensity ($d_{33}$) of Embodiment 6 is one having been patterned on the basis of the zeroth-order Bessel function as shown in FIG. 36. In particular, the Bessel function is defined on the piezoelectric element 5 in the same manner as in Embodiment 1, and the part where the Bessel function is negative is completely depolarized while, at the part where the Bessel function is positive, the degree of depolarization is determined in accordance with the magnitude thereof.

The thus obtained piezoelectric element 5 is assembled in the same manner as in Embodiment 1 to thereby obtain the transducer part 16 for ultrasonic probe.

The piezoelectric element 5 having the distribution of polarization intensity as shown in sections of FIGS. 36 and 37 can be obtained from the sectional structure of the piezoelectric ceramic 1 fabricated by partial depolarization with the use of laser beam 17 of the above constitution. In particular, the arrow 4 indicated in the section of the piezoelectric element 5 shown in FIG. 36 represents the intensity of polarization between broken line parts. The spontaneous polarization is large around the center, and the intensity of inter-electrode spontaneous polarization becomes lower as the distance to the periphery is decreased.

In Embodiment 6, the identical polarization direction is employed, so that the polarization intensity of any single piezoelectric element 5 can be expressed by the use of varied color density as shown in FIG. 37. In the piezoelectric element 5 of FIG. 37, the high color density indicates that the part has a high polarization intensity.

Figure 41:
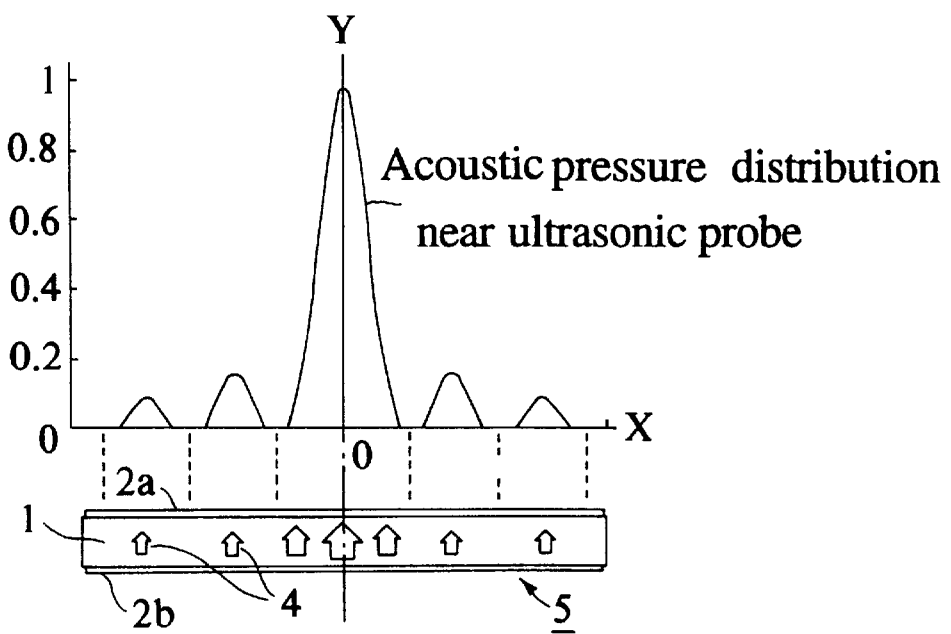
FIG. 41 is a view showing the acoustic pressure distribution near the ultrasonic probe according to Embodiment 6.

Application of voltage to the above piezoelectric element 5 causes the part where the polarization intensity is high to have an increased extent of deformation. When the transducer part 16 shown in FIG. 40 like that of Embodiment 1 is fabricated from the piezoelectric element 5 having its polarization intensity varied on the basis of the Bessel function and energizing pulses are applied to the above piezoelectric element 5 by a pulser not shown as in Embodiment 6, the distribution of intensity of the ultrasonic beam transmitted in the vicinity of the acoustic matching layer 7 approximates to the Bessel function. Naturally, in Embodiment 6, only the acoustic pressure distribution corresponding to the positive part of the zeroth-order Bessel function is transmitted as shown in FIG. 41. That is, what is transmitted is only the ultrasonic wave with the acoustic pressure distribution which is roughly approximate to the Bessel function, so that the effect as to the nondiffracting sound field is limited with the result that a sound field susceptible to diffusion as compared with that of Embodiment 1 is formed. However, Embodiment 6 ensures the following advantage. In the polarization of the piezoelectric element 5, polarization is carried out until the polarization intensity is saturated according to the customary procedure. Thus, the supervision of the polarization step is easy. The regulation and control of the intensity of laser beam for depolarization is easier than that of the polarization intensity, so that as a whole the piezoelectric element 5 capable of transmitting the Bessel sound field can be obtained by the easy steps.

FIG. 41 shows the relationship between hydrophone output voltage and polarization intensity (indicated by the arrow 4) obtained by measuring the acoustic pressure distribution in the vicinity of the ultrasonic probe fabricated in Embodiment 6 with the use of a hydrophone.

Modification 1 to Embodiment 6

High energy beams such as $CO_2$ laser and light beam from a light source, e.g., a halogen lump can be used instead of YAG laser employed in Embodiment 6.

Modification 2 to Embodiment 6

Although the atmosphere has been regulated by blowing nitrogen gas of about 0° C. onto the piezoelectric element 5 during the irradiation with laser beam 17 in Embodiment 6, naturally, the similar effect can be obtained by cooling with other gases. Further, the effect of avoiding the temperature rise at other than in the vicinity of the zone irradiated with laser beam 17 can be attained by the execution in a fluid such as silicone oil through which laser beam 17 can be passed without any danger.

The electrode material per se might be evaporated off at the time of heating by means of laser beam 17, depending on the type of the electrode material. In this case, it is suitable to effect connection with the use of a conductive resin or carry out re-connection by sputtering, vapor deposition or other appropriate method. Moreover, when the connection temperature is low so as to be free from adversely affecting the piezoelectricity, similar performance is attained by the use of other means such as solder or thermocompression bonding as long as electrical communication is ensured.

Although the zeroth-order Bessel function having two positive (+)-side hills and two negative (−)-side valleys on each side excluding the center is employed in Embodiment 6, the nondiffracting beam can be realized as long as there exist at least one positive (+)-side hill and at least one negative (−)-side valley on each side excluding the center to thereby enable obtaining the same effects as in Embodiment 6.

Although the acoustic matching layer 7 of Embodiment 6 is a monolayer structure of an epoxy resin, similar effects can naturally be exerted by, for example, an acoustic matching layer 7 having a double layer structure composed of an epoxy resin layer and a layer of an epoxy resin containing alumina or the like as a filler or an acoustic matching layer 7 having a three layer structure including a polyethylene layer, a layer of an epoxy resin compounded with some filler and a machinable ceramics layer.

The Bessel beam is known as a nondiffracting beam. Measuring the sound field of the transducer part 16 according to Embodiment 6 and measuring the beam width demonstrate that the zone where the beam width is narrow is very long, thereby ensuring the fabrication of an ultrasonic probe having a large optimum observation distance (depth of focus) having never been attained in the art. Therefore, an ultrasonic probe of high resolution can be fabricated in which use is made of a single coaxial cable and a single pulser so that the electrical circuit and the transducer part 16 have simple structures and are inexpensive.

Embodiment 7

The efficiency of the depolarization step of the steps of Embodiment 6 has been improved.

Parts to be depolarized of the polarized electrode of the piezoelectric element 5 are colored black as shown in FIG. 39. A black paint containing carbon is especially suitable for the coloring.

The electrode material is generally metallic, so that the reflection ratio is high, thereby causing the laser beam for depolarization to be reflected in a high ratio. Thus, long-time irradiation is inevitable for satisfactory depolarization, so that the efficiency is deteriorated in the input energy, period of time and number of steps.

Further, the problem is encountered that parts adjacent to the irradiated zone are also intensely heated to suffer from extensive depolarization because of heat conduction, thereby rendering it difficult to control the degree of depolarization.

Coloring parts to be depolarized black in advance as in Embodiment 7 is advantageous in that laser beam is effectively absorbed to thereby enable heating the desired position only.

In Embodiment 7, the zone at which the temperature is to be raised can easily be limited and the fabrication efficiency is enhanced.

Modification 1 to Embodiment 7

Figure 42:
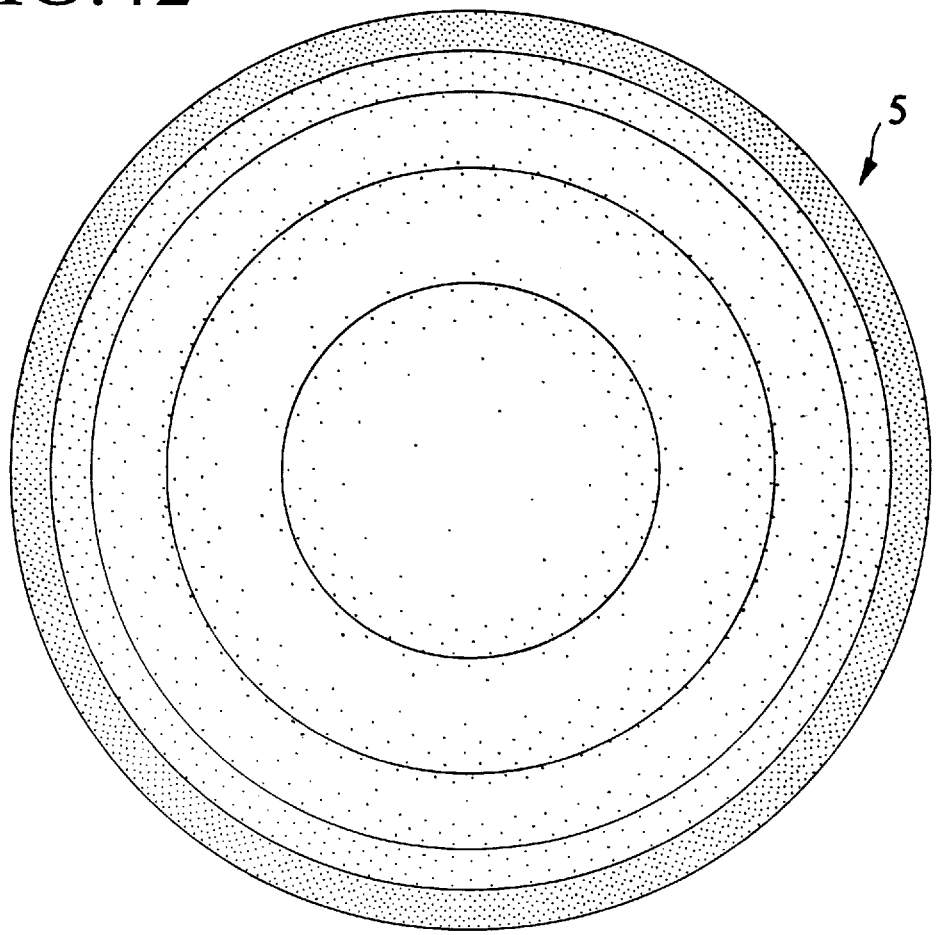
FIG. 42 is a view showing the coloring state of the piezoelectric element according to Embodiment 7.

Referring to FIG. 42, on the piezoelectric element 5, positions to be completely depolarized are colored thickly while positions where the polarization is to be weakened are colored thinly in conformity to the degree of weakening. Thickly colored parts readily absorb laser beam and effect temperature rise and, the thinner the coloring, the less the absorptivity of laser beam and the slower the temperature rise. This enables obtaining the piezoelectric element 5 having the desired spontaneous polarization distribution by virtue of the coloring density even when all the surface of the piezoelectric element 5 is scanned with laser beam of uniform intensity. The control of the coloring density can easily be realized by the use of the known printing technology. Further, the above renders it unnecessary to strictly regulate the intensity of laser beam in accordance with the irradiation position, so that the piezoelectric element 5 of Embodiment 7 can be obtained by an apparatus of inexpensive construction.

Modification 2 to Embodiment 7

Use is made of rectangular and elliptic piezoelectric elements 5. The Bessel function is defined on each piezoelectric element 5 in the same manner as in Embodiments 2 and 3, and parts to be depolarized are colored and irradiated with laser beam.

Embodiment 8

The piezoelectric element 5 of Embodiment 8 is fabricated in the following manner. First, the Bessel function is defined on the piezoelectric element 5 in the same manner as in Embodiment 1. Split electrodes 3 are provided on one side of the piezoelectric element 5 at places other than a line on which the value of the Bessel function is nil and its vicinity.

A full covering electrode 2 is provided on the other side. A polarization voltage is impressed between split electrodes 3 corresponding to positive region of the Bessel function and the full covering electrode 2 so that polarization is performed up to saturation of the spontaneous polarization. Subsequently, a voltage is impressed between split electrodes 3 corresponding to negative region of the Bessel function and the full covering electrode 2 so that polarization is performed up to saturation of the spontaneous polarization.

Figure 43:
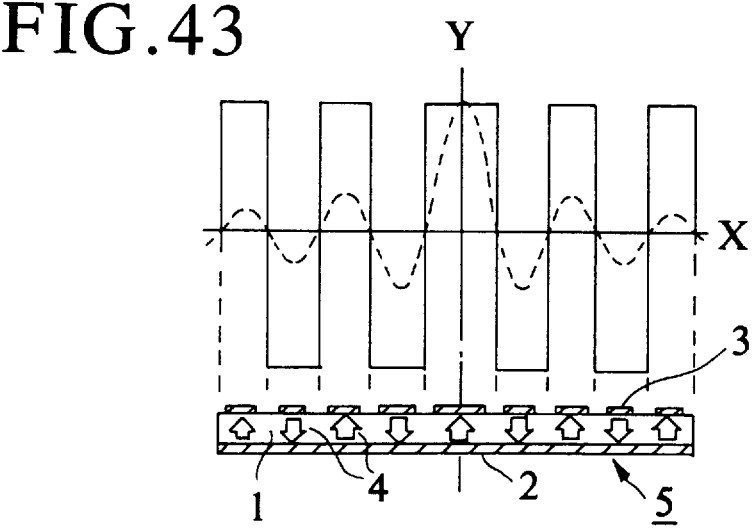
FIG. 43 is a view showing the spontaneous polarization distribution of the piezoelectric element according to Embodiment 8.

As a result, the spontaneous polarization is distributed as shown in FIG. 43. In FIG. 43, numerals 1 to 5 have the same meaning as in FIG. 36.

Subsequently irradiation with laser beam is carried out in the same manner as in Embodiment 6 to thereby regulate the spontaneous polarization distribution so as to obtain the same acoustic pressure distribution as the Bessel function shown by an undulating line in FIG. 43. Thereafter, the polarized split electrodes 3 are electrically connected to each other with the use of a conductive paste. The same transducer part 16 as in FIG. 40 is fabricated from the thus fabricated piezoelectric element 5 and used in an ultrasonic endoscope or the like.

In Embodiment 8, the same functions as in Embodiment 1 are exerted.

A spontaneous polarization distribution smoother than in Embodiments 1 to 6 is obtained in Embodiment 8, so that the ultrasonic sound field can be transmitted in the form of a smoother and more accurate Bessel function distribution. An accurate nondiffracting sound field is obtained to thereby reduce the diffusion of the ultrasonic wave and enable obtaining clearer ultrasonic image.

Modification 1 to Embodiment 8

Parts to be depolarized of the electrode of the piezoelectric element 5 may be colored black, and the coloring density may be varied in conformity to the degree of intended depolarization. The invention may be used in rectangular and elliptic piezoelectric elements 5 and also piezoelectric elements 5 for electronic scanning ultrasonic probe devices. Moreover, the electrodes may be in split form on both the top and the back of the piezoelectric element 5 at the time of executing polarization thereof.

Embodiment 9

Figure 44:
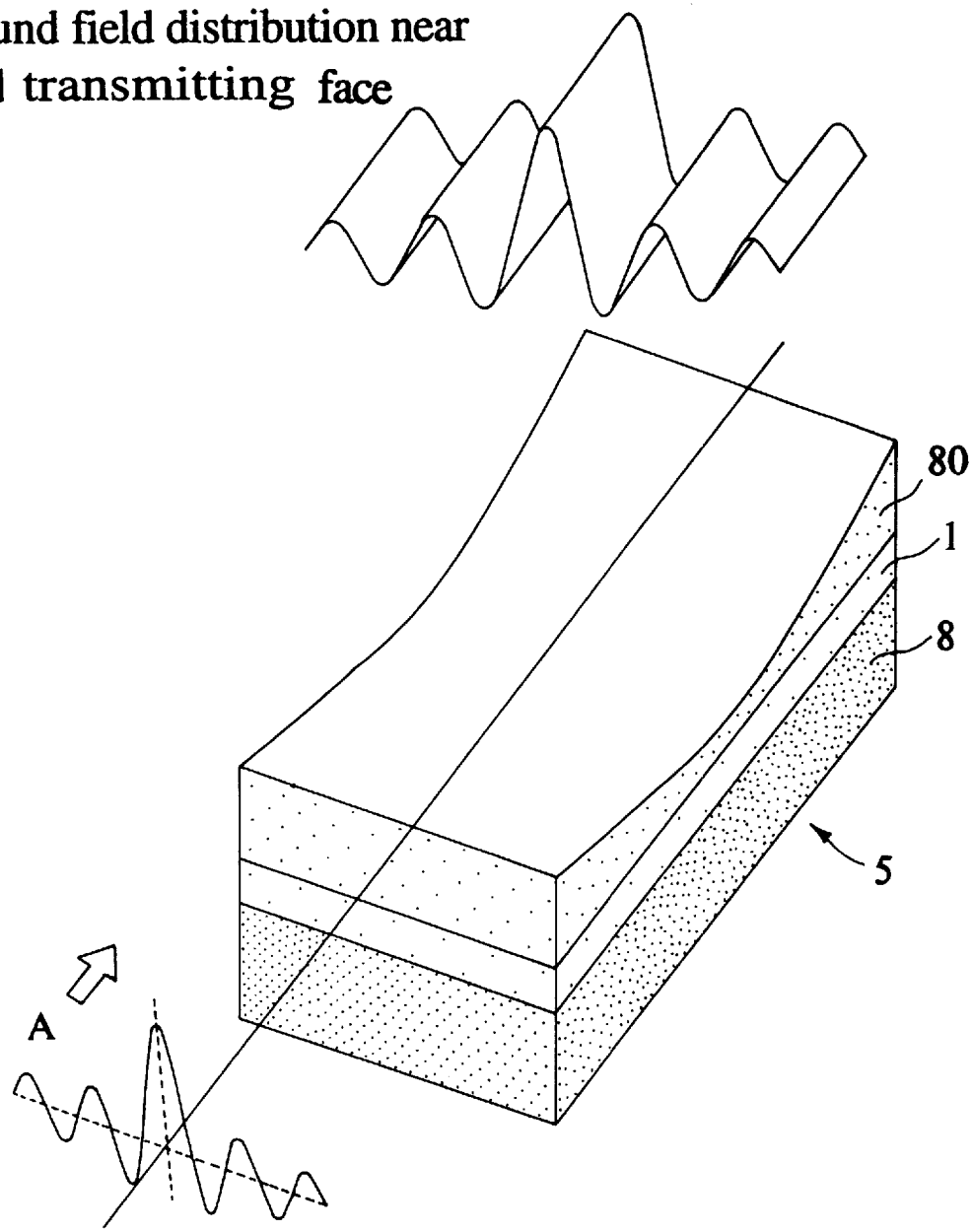
FIG. 44 is a view showing the piezoelectric element of Embodiment 9 and its sound field distribution.
Figure 45:
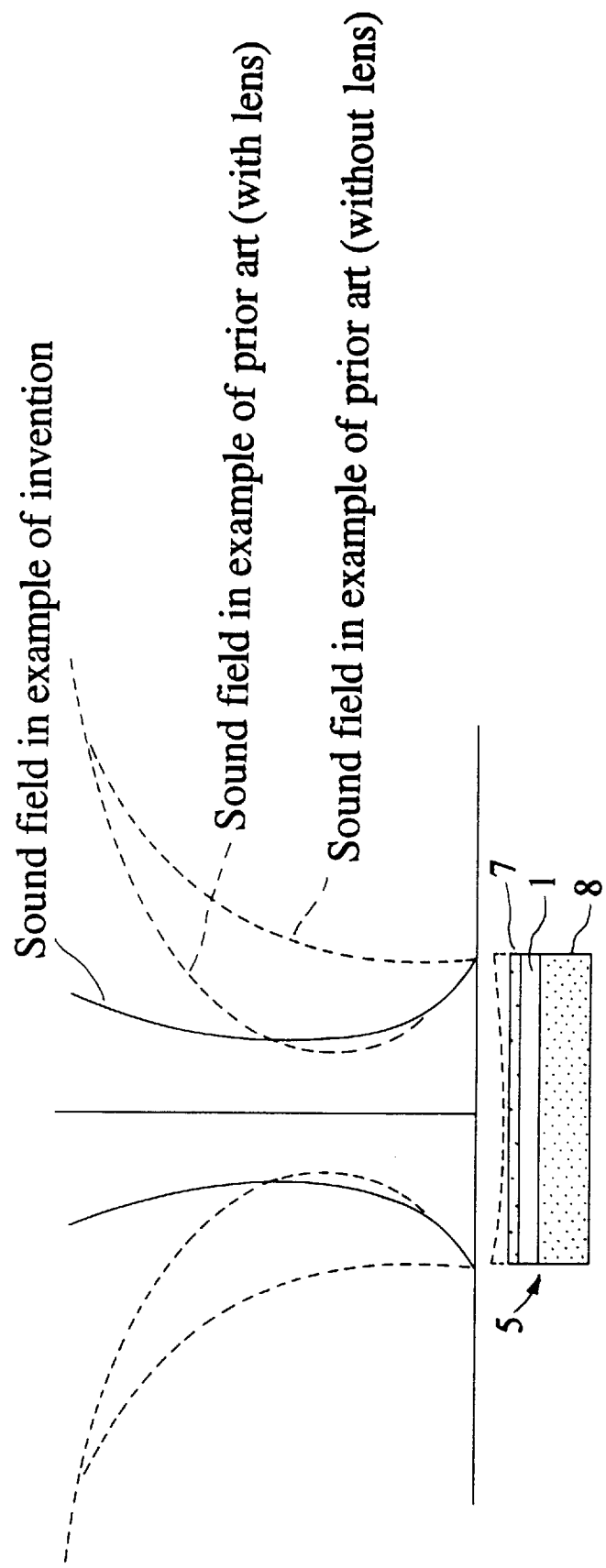
FIG. 45 is a view showing the sound field distribution viewed from the A-side of FIG. 44 according to Embodiment 9.

FIG. 44 shows the ultrasonic probe of Embodiment 9 and FIG. 45 shows the sound field viewed from the A-side of FIG. 44.

The Bessel function is defined on a short side of a rectangular piezoelectric element 5. Specifically, provided that the Bessel function of $J_0$ (x/a) (wherein a is a constant) is set on an axis parallel to a short side of the piezoelectric element 5 with the assumption of X-axis of coordinate having its origin at an middle point of the short side, a spontaneous polarization distribution is provided so that an acoustic pressure distributed in a profile resulting from parallel movement of the Bessel function along a long side of the piezoelectric element 5 is obtained. At that time, the electrode is split into stripes parallel to the long side and polarized until the state of saturation is reached in each of positive and negative directions. Thereafter, the electrode is colored, and the piezoelectric element 5 is partially depolarized to thereby obtain the desired polarization intensity.

A cylindrical acoustic lens capable of converging the ultrasonic wave in the direction of the long side is mounted on the thus obtained piezoelectric element 5. Further, a driving coaxial cable not shown is connected thereto. The resultant transducer part 16 for ultrasonic probe is used in a small-diameter ultrasonic probe device as shown in FIG. 18.

In the direction of short side of the piezoelectric element 5, the Bessel acoustic pressure distribution is obtained, so that a nondiffracting sound field can be obtained which does not diffuse during the propagation thereof as shown in FIG. 45. On the other hand, in the direction of long side of the piezoelectric element 5, the ultrasonic wave is converged by the acoustic lens 80. The aperture size relative to wavelength is large to thereby cause the diffusion to be less in the direction of long side as compared with that in the direction of short side.

In Embodiment 9, the splitting of the electrode and the configuration of the polarization are so simple that the invention can be applied to an ultrasonic probe device of an outer diameter as extremely minute as 2 mm or less.

Embodiment 10

Figure 46:
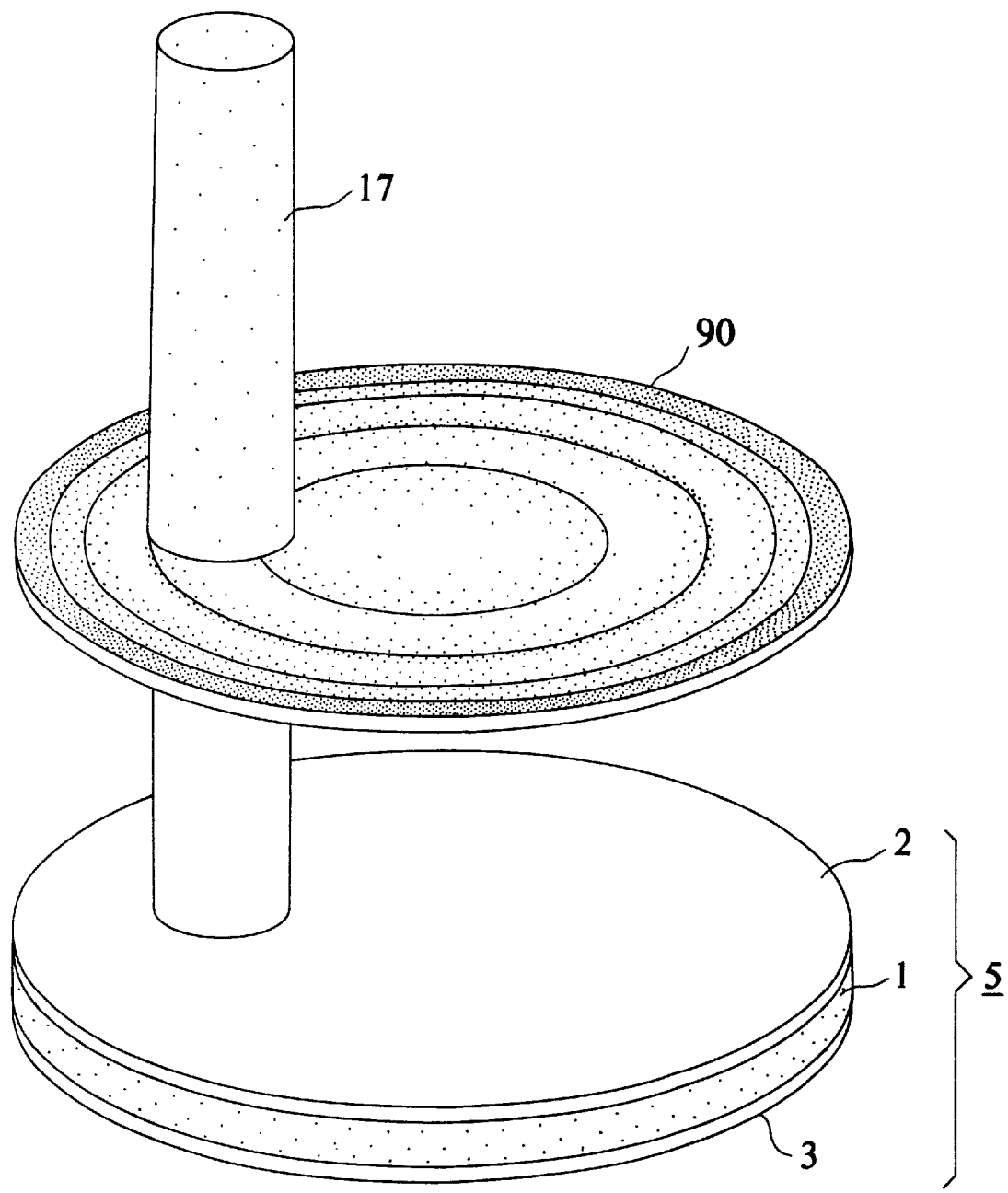
FIG. 46 is a view showing the process for producing the transducer part according to Embodiment 10.
Figure 47:
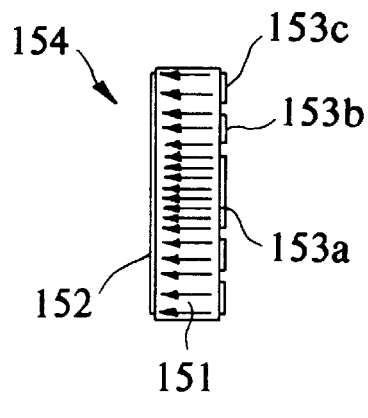
FIG. 47 is a sectional view showing the conventional piezoelectric element.
Figure 48:
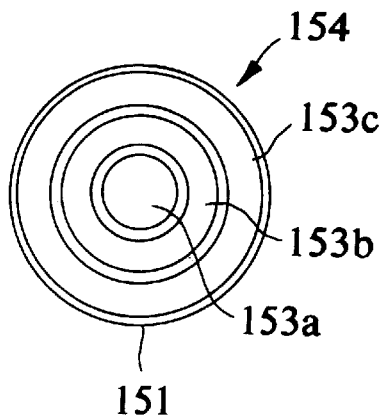
FIG. 48 is a plan showing the conventional piezoelectric element.

FIG. 46 shows the process for producing the transducer part 16 for ultrasonic probe according to Embodiment 10. In Embodiment 10, the efficiency of the depolarization step is enhanced out of the steps of Embodiment 6.

A mask 90 whose transmittance for laser beam is not uniform is interposed between the polarized piezoelectric element 5 and the laser source. The piezoelectric element 5 is irradiated through the mask 90 with laser beam 17. The mask 90 is composed of an optical material having high transmittance for laser beam which has been patterned with a highly reflective material such as silver. The mask 90 is formed so that the transmittance is high where laser beam 17 with which parts to be depolarized of the piezoelectric element 5 are irradiated passes through the mask, that the reflectivity is high at positions corresponding to the parts not to be depolarized and that the reflection is complete at positions corresponding to the parts entirely not to be depolarized.

The temperature of the parts of the piezoelectric element 5 irradiated with laser beam of high intensity having passed through the mask 90 at positions of high transmittance is easily raised, while the temperature rise is slow at the parts of the piezoelectric element 5 irradiated with laser beam of low intensity having passed through the mask 90 at positions of low transmittance.

The piezoelectric element 5 having the desired spontaneous polarization distribution can be obtained by virtue of the transmittance distribution of the mask 90 even when all the surface of the piezoelectric element 5 is scanned with laser beam 17 of uniform intensity. The control of the transmittance distribution can easily be realized by the use of the known film forming technology. In Embodiment 10, it is unnecessary to strictly regulate the intensity of laser beam 17 in accordance with the irradiation position, so that the above piezoelectric element 5 can be obtained by an apparatus of inexpensive construction.

Modification 1 to Embodiment 10

The invention is also applicable to the instance in which spontaneous polarization of the opposite direction is involved as in Embodiment 8 like Embodiment 7 as mentioned above and to the exclusively unidirectional linear spontaneous polarization distribution as in Embodiment 9.

What is claimed is:

1. An ultrasonic probe adapted to transmit and receive an ultrasonic wave, comprising:

a coaxial cable capable of transferring an energizing pulse voltage and an echo signal;

at least one piezoelectric element having two principal surfaces provided with both active and ground electrodes, wherein at least one of the electrodes is split into electrode parts, each of which connects, together with other electrode parts belonging to the same principal surface, with one of an outer conductor and an inner conductor of said coaxial cable;

an acoustic matching layer disposed on a sound transmitting face side of each piezoelectric element; and an acoustic backing layer disposed on its opposite side;

wherein each piezoelectric element has differences in intensity of spontaneous polarization according to positions of the piezoelectric element as defined below:

a distribution of the intensity of spontaneous polarization is determined so that an acoustic pressure distribution from the probe is as follows:

provided that a straight line at right angles to a geometric symmetry axis is selected on a surface of the piezoelectric element and designated as X-axis, said X-axis having an origin which is an intersection of the X-axis and the geometric symmetry axis of the piezoelectric element, the zeroth-order Bessel function $Y=J_0$ (x/a), wherein a is an arbitrary constant, is drawn along said X-axis, so that the value of $J_0$ (x/a) at each position of the X-axis is caused to correspond to a sign (positive or negative) and magnitude of acoustic pressure transmitted from the position upon application of an energizing pulse, namely, the spontaneous polarization is caused to be strong at a position where the absolute value of $J_0$ (x/a) is large while the spontaneous polarization is weak at a position where the absolute value of $J_0$ (x/a) is small, so that the spontaneous polarization at a position where the $J_0$ (x/a) is positive has a direction opposite to that of the spontaneous polarization at a position where the $J_0$ (x/a) is negative, so that the piezoelectric element has a distribution of intensity of spontaneous polarization which is linearly symmetrical or axially symmetrical on its axis of symmetry, and so that the direction of the spontaneous polarization is substantially perpendicular to the two principal surfaces throughout the surfaces of the piezoelectric element.

2. The ultrasonic probe according to claim 1 wherein at least one surface of each piezoelectric element has an electrode split along a contour of acoustic pressure distribution to be obtained and wherein the split electrode parts are electrically connected with each other.

3. The ultrasonic probe according to claim 2, wherein use is made of a piezoelectric element having at least a split line of electrode along a zero position of contour of acoustic pressure distribution to be obtained.

4. The ultrasonic probe according to claim 2, wherein splitting into a plurality of electrodes is effected at one or more points of a part where acoustic pressure distributions to be obtained are in the same phase.

5. An ultrasonic probe device comprising an insertion part and, arranged in a tip thereof, the ultrasonic probe as claimed in claim 1.

6. The ultrasonic probe device according to claim 5, wherein the insertion part is flexible.

7. The ultrasonic probe device according to claim 5, wherein the insertion part is rigid.

8. An ultrasonic probe adapted to transmit and receive an ultrasonic wave, comprising:

a coaxial cable capable of transferring an energizing pulse voltage and an echo signal;

at least one piezoelectric element having two principal surfaces provided with both active and ground electrodes, wherein at least one of the electrodes is split into electrode parts, each of which connects, together with other electrode parts belonging to the same principal surface, with one of an outer conductor and an inner conductor of said coaxial cable;

an acoustic matching layer disposed on a sound transmitting face side of each piezoelectric element; and an acoustic backing layer disposed on its opposite side;

wherein each piezoelectric element has differences in intensity of spontaneous polarization according to positions of the piezoelectric element, said spontaneous polarization having a direction substantially perpendicular to two principal surfaces throughout the surfaces of the piezoelectric element, and wherein a distribution of the intensity of spontaneous polarization is determined so that an acoustic pressure distribution from the probe is as follows:

provided that a straight line at right angles to a geometric symmetry axis is selected on a surface of the piezoelectric element and designated as X-axis, said X-axis having an origin which is an intersection of the X-axis and the geometric symmetry axis of the piezoelectric element, the zeroth-order Bessel function $Y=J_0$ (x/a), wherein a is an arbitrary constant, is drawn along said X-axis, said Bessel function being step approximated so that the step approximated value of $J_0$ (x/a) at each position of the X-axis is caused to correspond to a sign (positive or negative) and magnitude of acoustic pressure transmitted from the position upon application of an energizing pulse, namely, the spontaneous polarization is caused to be strong at a position where the step approximated value of $J_0$ (x/a) is large while the spontaneous polarization is weak at a position where the step approximated value of $J_0$ (x/a) is small, so that the spontaneous polarization at a position where the step approximated $J_0$ (x/a) is positive has a direction opposite to that of the spontaneous polarization at a position where the step approximated $J_0$ (x/a) is negative, and so that the piezoelectric element has a distribution of intensity of spontaneous polarization which is linearly symmetrical or axially symmetrical on its axis of symmetry.

9. The ultrasonic probe according to claim 1 or 8, wherein each piezoelectric element has a circular shape having its intensity of spontaneous polarization distributed in the form of concentric circles.

10. The ultrasonic probe according to claim 1 or 8, wherein each piezoelectric element has a rectangular shape having its intensity of spontaneous polarization determined as follows:

provided that the rectangle has two sides each having a length of s and two sides each having a length of t, that the rectangle has its center, i.e., intersection of diagonal lines agreeing with the origin of the X-Y coordinate system and that two sides of the rectangle are parallel to the X-axis while the other two sides are parallel to the Y-axis, the intensity of spontaneous polarization is determined so that an acoustic pressure is transmitted being proportional to $J_0$ (X*s*a) when point (X, Y) is present within a triangle including the origin and consisting of lines each having a length of s and $J_0$ (Y*t*a) when point (X, Y) is present within a triangle including the origin and consisting of lines each having a length of t, namely, having a contour of similar square morphologies with identical geometric centers.

11. The ultrasonic probe according to claim 1 or 8, wherein each piezoelectric element has an elliptic shape having its intensity of spontaneous polarization determined as follows:

provided that the ellipse has a major axis having a length of s and a minor axis having a length of t, that the ellipse has its center, i.e., middle point of two focuses agreeing with the origin of the X-Y coordinate system and that the major axis and the minor axis of the ellipse are caused to agree with the X-axis and the Y-axis, respectively, the distribution of spontaneous polarization is determined so that an acoustic pressure with a profile obtained by enlarging the Bessel distribution of the circular piezoelectric electric element by a factor of s/t in the direction of the Y-axis is transmitted.

12. The ultrasonic probe according to claim 1 or 8, wherein each piezoelectric element has a rectangular shape having its intensity of spontaneous polarization determined as follows:

provided that the Bessel function of $J_0$ (x/a) (wherein a is a constant) is set on an axis parallel to a side of one small element of each piezoelectric element with the assumption of X-axis of coordinate having its origin at an middle point of said side of the small element, spontaneous polarization is given so that an acoustic pressure distributed in a profile resulting from parallel movement of the Bessel function along another side of the small element is obtained.

13. The ultrasonic probe according to claim 12, wherein the side defining the axis is a long side.

14. An ultrasonic probe for electronic scanning ultrasonic diagnostic equipments which comprises piezoelectric elements employed in claim 13, said piezoelectric elements being arranged in a single row in a fashion such that the long sides thereof neighbor to each other.

15. The ultrasonic probe according to claim 14, wherein the piezoelectric elements are linearly arranged in a single straight line.

16. The ultrasonic probe according to claim 14, wherein the piezoelectric elements are arranged in convex form.

17. The ultrasonic probe according to claim 14, wherein the piezoelectric elements are arranged in radial form.

18. An ultrasonic diagnostic equipment comprising the ultrasonic probe as claimed in any one of claims 14 to 17 to which energizing pulses of identical polarity and voltage are applied with varied timings to thereby conduct electronic focusing.

19. An ultrasonic diagnostic equipment having an electronic convex or electronic radial scanning ultrasonic probe connected thereto in which energizing pulses of varied polarity and magnitude are applied to a plurality of piezoelectric elements used for forming a single acoustic beam with timings such that formed ultrasonic wave front is in a plane perpendicular to an acoustic axis.

20. The ultrasonic diagnostic equipment according to claim 19, wherein the polarity and magnitude of the energizing pulse applied to each piezoelectric element are determined as follows:

provided that small elements employed for forming a single acoustic beam are designated as one block, that Y-axis is set in the direction of arrangement of the small elements with the use of a geometric center of the one block as an origin of the Y-axis and that the zeroth-order Bessel function of $J_0$ (y/b) wherein b is a constant is assumed along the Y-axis, values of the zeroth-order Bessel function are averaged every small-element length, the average value being designated as a target acoustic pressure to be transmitted by each small element and energizing pulse voltage and its polarity are controlled so as to transmit the above target acoustic pressure with the use of the facts that driving of each piezoelectric element at a high voltage leads to transmission of a high acoustic pressure while driving thereof at a low voltage leads to transmission of a low acoustic pressure and that conversion of the polarity of the energizing pulse causes the transmitted acoustic pressure to have a conversed phase.

21. A process for producing the piezoelectric element having a Bessel distribution of polarization intensity as employed in claim 20, which comprises polarizing a piezoelectric element to saturation followed by partial depolarization.

22. An ultrasonic diagnostic system comprising an ultrasonic probe as claimed in claim 13 wherein, as a small element forming the ultrasonic probe, use is made of a piezoelectric element of a rectangular shape having its intensity of spontaneous polarization determined as follows:

provided that the Bessel function of $J_0$ (x/a) (wherein a is a constant) is set on an axis parallel to a side of one small element of each piezoelectric element with the assumption of X-axis of coordinate having its origin at an middle point of said side of the small element, spontaneous polarization is given so that an acoustic pressure distributed in a profile resulting from parallel movement of the Bessel function along another side of the small element is obtained, and wherein application of a driving acoustic pressure to each element of a block forming a single acoustic beam with the use of the ultrasonic probe is performed as in claim 20.

23. The ultrasonic diagnostic system according to claim 22, wherein, provided that one block has an element width (length of small element) of s and a length of t, the values of constants a and b are determined so as to satisfy the equality b=ta/s.

24. The ultrasonic probe according to claim 12, wherein the side defining the axis is a short side.

25. A process for producing the piezoelectric element having a Bessel distribution of polarization intensity as employed in claim 8, which comprises polarizing a piezoelectric element to saturation followed by partial depolarization.

26. An ultrasonic diagnostic equipment having an electronic linear scanning ultrasonic probe connected thereto in which energizing pulses of varied polarity and magnitude are applied with identical timings to a plurality of piezoelectric elements used for forming a single acoustic beam.

27. The ultrasonic diagnostic equipment according to claim 26, wherein the polarity and magnitude of the energizing pulse applied to each piezoelectric element are determined as follows:

provided that a row of small elements employed for forming a single acoustic beam are designated as one block and that the zeroth-order Bessel function of $J_0$ (y/b) wherein b is a constant is assumed along Y-axis, values of the zeroth-order Bessel function are averaged every small-element length, the average value being designated as a target acoustic pressure to be transmitted by each small element, and energizing pulse voltage and its polarity are controlled so as to transmit the above target acoustic pressure with the use of the facts that driving of each piezoelectric element at a high voltage leads to transmission of a high acoustic pressure while driving thereof at a low voltage leads to transmission of a low acoustic pressure and that conversion of the polarity of the energizing pulse causes the transmitted acoustic pressure to have a conversed phase.

28. An ultrasonic diagnostic system comprising an ultrasonic probe as claimed in claim 13 wherein, as a small element forming the ultrasonic probe, use is made of a piezoelectric element of a rectangular shape having its intensity of spontaneous polarization determined as follows:

provided that the Bessel function of $J_0$ (x/a) (wherein a is a constant) is set on an axis parallel to a side of one small element of each piezoelectric element with the assumption of X-axis of coordinate having its origin at an middle point of said side of the small element, spontaneous polarization is given so that an acoustic pressure distributed in a profile resulting from parallel movement of the Bessel function along another side of the small element is obtained, and wherein application of a driving acoustic pressure to each element of a block forming a single acoustic beam with the use of the ultrasonic probe is performed as in claim 27.

29. The ultrasonic diagnostic system according to claim 28, wherein, provided that one block has an element width (length of small element) of s and a length of t, the values of constants a and b are determined so as to satisfy the equality b=ta/s.

30. An ultrasonic probe comprising a cable capable of transferring an energizing pulse voltage and an echo signal and at least one piezoelectric element, each piezoelectric element having differences in intensity of spontaneous polarization according to positions of the piezoelectric element, wherein at least one surface of each piezoelectric element has an electrode split along a contour of acoustic pressure distribution to be obtained from the piezoelectric element and wherein the split electrode parts are electrically connected with each other.

31. The ultrasonic probe according to claim 30 wherein use is made of a piezoelectric element having at least a split line of electrode along a zero position of contour of acoustic pressure distribution to be obtained.

32. The ultrasonic probe according to claim 30 wherein splitting into a plurality of electrodes is effected at one or more points of a part where acoustic pressure distributions to be obtained are in the same phase.

33. The ultrasonic probe according to any one of claims 30 to 32, wherein the split electrode parts are mutually electrically connected by applying a thin conductive film so as to cover a part or all of inter-electrode surface.

34. The ultrasonic probe according to any one of claims 30 to 32, wherein a split electrode surface is arranged on a side not agreeing with a sound transmitting face side.

35. The ultrasonic probe according to any one of claims 30 to 32, wherein an acoustic backing layer composed of a conductive material is arranged on a side of each piezoelectric element not agreeing with its sound transmitting face side, split electrodes are disposed on the side of the acoustic backing layer and the electrodes split by the acoustic backing layer are electrically connected with each other.

36. The ultrasonic probe according to any one of claims 30 to 32, wherein the split electrode parts are mutually connected with at least one linear conductor.

37. An ultrasonic probe device comprising an insertion part and, arranged in a tip thereof, the ultrasonic probe as claimed in claim 30.

38. An ultrasonic probe device comprising an insertion part and, arranged in a tip thereof, the ultrasonic probe as claimed in claim 8.

39. The ultrasonic probe according to claim 8, wherein at least one surface of each piezoelectric element has an electrode split along a contour of acoustic pressure distribution to be obtained and wherein the split electrode parts are electrically connected with each other.

40. A process for producing the piezoelectric element having a Bessel distribution of polarization intensity as employed in claim 20, which comprises polarizing a piezoelectric element to saturation followed by partial depolarization.

41. A process for producing a piezoelectric element, which comprises polarizing a piezoelectric element to saturation followed by partial depolarization so as to obtain a piezoelectric element suitable for use in ultrasonic probes which has differences in intensity of spontaneous polarization according to positions of the piezoelectric element as defined below;

a distribution of the intensity of spontaneous polarization is determined so that an acoustic pressure distribution from the probe is as follows:

provided that a straight line at right angles to a geometric symmetry axis is selected on a surface of the piezoelectric element and designated as X-axis, said X-axis having an origin which is an intersection of the X-axis and the geometric symmetry axis of the piezoelectric element, the zeroth-order Bessel function $Y=J_0(x/a)$, wherein a is an arbitrary constant, is drawn along said X-axis, so that the value of $J_0(x/a)$ at each position of the X-axis is caused to correspond to a sign (positive or negative) and magnitude of acoustic pressure transmitted from the position upon application of an energizing pulse, namely, the spontaneous polarization is caused to be strong at a position where the absolute value of $J_0(x/a)$ is large while the spontaneous polarization is weak at a position where the absolute value of $J_0(x/a)$ is small, so that the spontaneous polarization at a position where the $J_0(x/a)$ is positive has a direction opposite to that of the spontaneous polarization at a position where the $J_0(x/a)$ is negative, so that the piezoelectric element has a distribution of intensity of spontaneous polarization which is linearly symmetrical or axially symmetrical on its axis of symmetry, and so that the direction of the spontaneous polarization is substantially perpendicular to the two principal surfaces throughout the surfaces of the piezoelectric element.

42. A process for producing a piezoelectric element, which comprises polarizing a piezoelectric element to saturation and applying energy beams to a part of the piezoelectric element having been polarized to saturation to thereby effect partial depolarization so as to obtain a piezoelectric element suitable for use in ultrasonic probes which has differences in intensity of spontaneous polarization according to positions of the piezoelectric element as defined below:

a distribution of the intensity of spontaneous polarization is determined so that an acoustic pressure distribution from the probe is as follows:

provided that a straight line at right angles to a geometric symmetry axis is selected on a surface of the piezoelectric element and designated as X-axis, said X-axis having an origin which is an intersection of the X-axis and the geometric symmetry axis of the piezoelectric element, the zeroth-order Bessel function $Y=J_0(x/a)$, wherein a is an arbitrary constant, is drawn along said X-axis, so that the value of $J_0(x/a)$ at each position of the X-axis is caused to correspond to a sign (positive or negative) and magnitude of acoustic pressure transmitted from the position upon application of an energizing pulse, namely, the spontaneous polarization is caused to be strong at a position where the absolute value of $J_0(x/a)$ is large while the spontaneous polarization is weak at a position where the absolute value of $J_0(x/a)$ is small, so that the spontaneous polarization at a position where the $J_0(x/a)$ is positive has a direction opposite to that of the spontaneous polarization at a position where the $J_0(x/a)$ is negative, so that the piezoelectric element has a distribution of intensity of spontaneous polarization which is linearly symmetrical or axially symmetrical on its axis of symmetry, and so that the direction of the spontaneous polarization is substantially perpendicular to the two principal surfaces throughout the surfaces of the piezoelectric element.

43. The process according to claim 42, wherein any of light beams emitted from YAG laser, $CO_2$ laser and halogen lamps as light sources were used as the energy beams.

44. A piezoelectric element employed in claim 42 having a position to be depolarized colored on an electrode on at least one side thereof.

45. A process for producing the piezoelectric element as employed in claim 42, which comprises controlling conditions for irradiation with energy beams to thereby control a degree of depolarization.

46. An energy control method employed in claim 42 which comprises effecting energy control by means of a semitransmittable substance whose transmittance for energy beams is nonuniform or a process for producing a piezoelectric element which comprises applying said energy control method.

* * * * *